(12) United States Patent
Mitchell et al.

(10) Patent No.: US 12,070,216 B2
(45) Date of Patent: *Aug. 27, 2024

(54) VENTRICULAR ASSIST ASSEMBLY, SYSTEM, AND METHOD

(71) Applicant: The Regents of the University of Colorado, a body corporate, Denver, CO (US)

(72) Inventors: Max Bannister Mitchell, Castle Pines, CO (US); Alexander Travis Brown, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/845,700

(22) Filed: Jun. 21, 2022

(65) Prior Publication Data
US 2023/0008312 A1    Jan. 12, 2023

Related U.S. Application Data

(63) Continuation of application No. 16/414,154, filed on May 16, 2019, now Pat. No. 11,364,376, and a continuation of application No. 16/184,452, filed on Nov. 8, 2018, now Pat. No. 10,335,527.

(51) Int. Cl.
| | | |
|---|---|---|
| A61B 17/11 | (2006.01) | |
| A61M 60/148 | (2021.01) | |
| A61M 60/178 | (2021.01) | |
| A61M 60/863 | (2021.01) | |

(52) U.S. Cl.
CPC ............ *A61B 17/11* (2013.01); *A61M 60/148* (2021.01); *A61M 60/178* (2021.01); *A61M 60/863* (2021.01); *A61B 2017/1107* (2013.01); *A61M 2205/0216* (2013.01)

(58) Field of Classification Search
CPC ................ A61M 1/1008; A61M 1/122; A61M 2205/0216; A61M 2210/125; A61M 2205/0266; A61B 17/11; A61B 2017/1107; A61B 2017/00252; A61B 2017/1139

See application file for complete search history.

(56) References Cited

U.S. PATENT DOCUMENTS

| | | | | |
|---|---|---|---|---|
| 5,843,088 A | * | 12/1998 | Barra ................... | A61M 60/178 606/1 |
| 5,976,183 A | * | 11/1999 | Ritz ...................... | A61F 2/2409 623/2.11 |
| 6,146,325 A | * | 11/2000 | Lewis ................... | A61M 60/40 600/16 |

\* cited by examiner

*Primary Examiner* — Scott M. Getzow
(74) *Attorney, Agent, or Firm* — Rosenbaum IP, P.C.; David G. Rosenbaum

(57) ABSTRACT

An implantable anastomotic assembly, which is configured to be attached to cardiovascular tissue, includes a connection interface, a plurality of outer plates, and a plurality of connectors configured to extend between and interconnect the connection interface and the plurality of outer plates, respectively, according to various embodiments. The connection interface is separate from and non-contiguous with the plurality of outer plates, according to various embodiments.

16 Claims, 28 Drawing Sheets

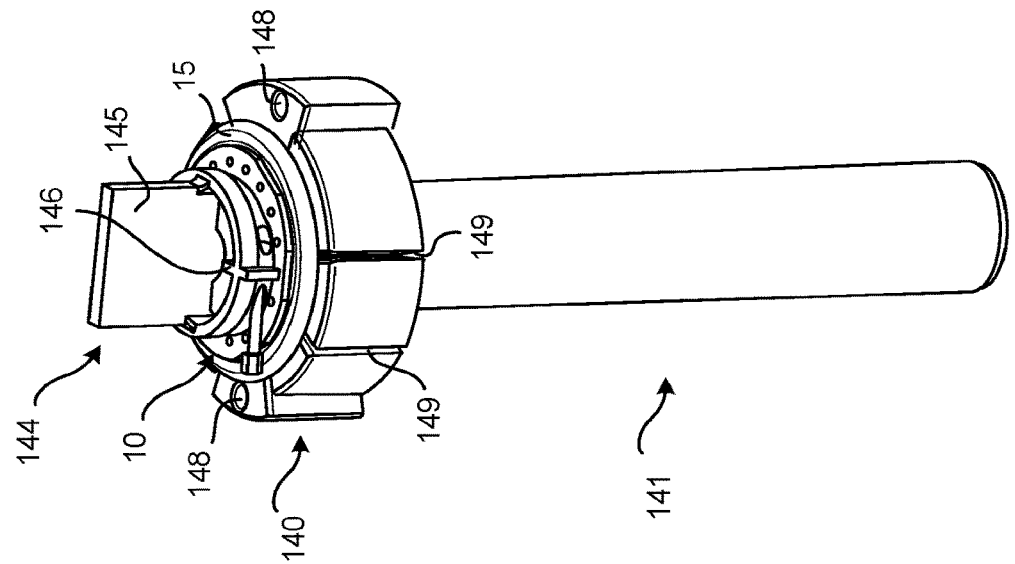
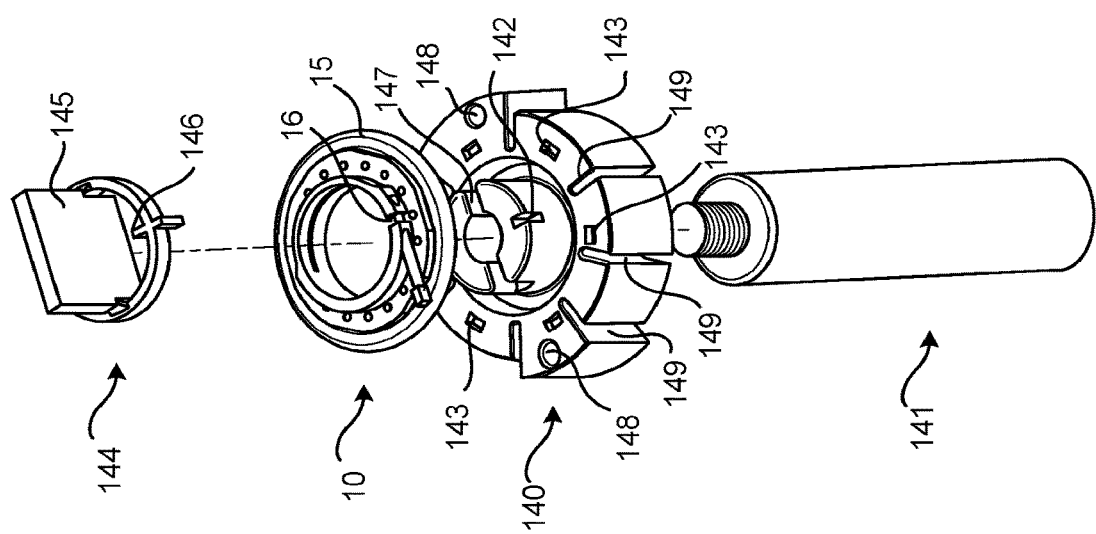
FIG. 7B
FIG. 7A

VENTRICULAR ASSIST ASSEMBLY, SYSTEM, AND METHOD

CROSS-REFERENCE TO RELATED APPLICATIONS

This application is a continuation of U.S. patent application Ser. No. 16/414,154, filed May 16, 2019, now U.S. Pat. No. 11,634,376, which is a continuation of U.S. Ser. No. 16/184,452, filed Nov. 8, 2018, now U.S. Pat. No. 10,335,527, which claims priority to U.S. Provisional Patent Application Ser. No. 62/583,030, filed on Nov. 8, 2017.

FIELD

The present disclosure relates to surgical devices, systems, and methods, and more particularly to ventricular assist devices, systems, and methods.

BACKGROUND

Heart failure is a leading cause of death in developed countries. An estimated 100,000 Americans develop end-stage congestive heart failure each year with a one-year mortality of approximately 50%. There are many etiologies of heart failure. Treatment options depend on the underlying cause and consist of drug therapy, catheter based or surgical interventions for coronary artery disease, and catheter or surgical procedures for valve disease and other lesions. In the past, the only treatment for end-stage non-correctable heart failure was heart transplantation. Approximately 2,000 heart transplant procedures are done annually in the United States and approximately 5,000 are performed annually world-wide. At any given time, there are approximately 3,000 patients on the heart transplant waiting list in the United States. Consequently, demand for transplantation far outstrips the supply of donor hearts, and it is unlikely that this supply imbalance will improve. Because of the donor supply imbalance, practitioners have developed mechanical systems to support the circulation in patients with heart failure at imminent risk of death.

These systems are known as ventricular assist systems ("VAS") or more commonly as ventricular assist devices ("VAD"). A VAD implemented on the left side of the heart is referred to as a left ventricular assist device ("LVAD"), right side devices are referred to as right ventricular assist devices ("RVAD"s), and when applied to both sides of the heart these devices are referred to as "Bi-VAD" s. Initially, VAD therapy was limited to heart transplant candidates and was intended to buy time for these patients to survive to transplant and to improve their baseline health status going into transplant. This strategy is commonly referred to as Bridge to Transplant ("BTT"). As technology improved, VAD outcomes improved dramatically and VAD therapy was extended to the much larger population of heart failure patients who are not candidates for transplant. VAD treatment in the latter pool of patients with heart failure is referred to as Destination Treatment ("DT").

Conventional LVADs include pulsatile devices that create a pulsed flow and non-pulsatile devices that provide continuous flow. Most current LVADs are continuous flow devices. The smaller continuous flow LVADs are placed within the pericardial space and do not require an intra-abdominal pocket. These devices generally employ a separate component, called an apical cuff, that is first attached to the left ventricular apex, and the pumping device is then attached to the apical cuff. Most conventional apical cuffs consist of a rigid metal cylinder surrounded by a fabric sewing ring.

Conventional installation methods for apical cuffs generally involve attaching the apical cuff to the left ventricular apex with surgically placed sutures that are brought through the sewing ring on the apical cuff. For example, a practitioner may utilize a plurality of horizontal mattress double-armed pledgeted sutures placed from the epicardial surface of the left ventricular myocardium toward the sewing ring on the apical cuff. Each needle is passed through the heart and then up through the sewing ring. After all sutures are placed, the sutures are successively tied resulting in knots on the sewing ring. After the apical cuff is attached to the heart, a core of left ventricular muscle is removed in the center of the apical cuff and the pump is mechanically fastened to the apical cuff. This conventional method/practice of placing pledgeted sutures is time consuming, and imperfections may result in significant bleeding complications.

SUMMARY

In various embodiments, the present disclosure provides one or more surgical devices, systems, and methods that address one or more of the above mentioned shortcomings. In various embodiments, the present disclosure provides an implantable anastomotic assembly that is configured to be attached to cardiovascular tissue. The implantable anastomotic assembly includes a connection interface, a plurality of outer plates, and a plurality of connectors configured to extend between and interconnect the connection interface and the plurality of outer plates, respectively, according to various embodiments. An outer plate of the plurality of outer plates is configured to be engaged against the cardiovascular tissue before a respective connector of the plurality of connectors is interconnected between the connection interface and the outer plate of the plurality of outer plates, according to various embodiments.

In various embodiments, the connection interface defines a plurality of apertures, each outer plate of the plurality of outer plates defines a receptacle, and each connector of the plurality of connectors is configured to be inserted through a respective aperture of the plurality of apertures of the connection interface and to engage with the receptacle of a respective outer plate of the plurality of outer plates. The plurality of connectors may comprise superelastic material. In various embodiments, each connector of the plurality of connectors includes a distal end having one or more retention features configured to engage the receptacle of the respective outer plate of the plurality of outer plates. In various embodiments, each connector of the plurality of connectors includes a proximal end comprising a tab configured to engage the connection interface adjacent the respective aperture. In various embodiments, the plurality of connectors are configured to extend through the cardiovascular tissue.

In various embodiments, the plurality of connectors are configured to extend outside of the cardiovascular tissue. For example, each connector of the plurality of connectors may include a connection tab, the connection tab may extend from the connection interface, and the respective outer plate may comprise a ratcheting mechanism configured to receive a portion of the connection tab.

In various embodiments, the connection interface includes a support ring that is configured to be engaged against an apical cuff of a ventricular assist device. In various embodiments, each outer plate of the plurality of outer plates includes one or more tines for insertion into the cardiovascular tissue. In various embodiments, each outer plate of the plurality of outer plates is an arcuate segment having a concave surface configured to engage the cardiovascular tissue.

Also disclosed herein, according to various embodiments, is a method of attaching an implantable anastomotic assembly to cardiovascular tissue. The method may include engaging a connection interface against the cardiovascular tissue, engaging an outer plate against the cardiovascular tissue a distance away from the connection interface, and after engaging the connection interface and the outer plate against the cardiovascular tissue, interconnecting the connection interface to the outer plate using a connector. In various embodiments, before interconnecting the connection interface and the outer plate, the connection interface is separate from and non-contiguous with the outer plate.

In various embodiments, interconnecting the connection interface to the outer plate comprises inserting the connector through the cardiovascular tissue. The method may further include, after engaging the connection interface against the cardiovascular tissue and after engaging the outer plate against the cardiovascular tissue but before interconnecting the connection interface and the outer plate, approximating the outer plate relative to the connection interface. In various embodiments, the connection interface comprises a support ring and the method includes, before engaging the connection interface against the cardiovascular tissue, coupling the support ring to an apical cuff of a ventricular assist device. Coupling the support ring to the apical cuff may include inserting a distal end of the connector at least partially into a sewing ring of the apical cuff.

In various embodiments, wherein inserting the connector through the cardiovascular tissue includes inserting the connector through an aperture defined in the connection interface and engaging the distal end of the connector to a receptacle of the outer plate. The connector may comprise a superelastic material, and inserting the connector through the cardiovascular tissue may include allowing the connector to transition from a pre-installed longitudinal shape to an installed longitudinal shape. In various embodiments, before inserting the connector through the cardiovascular tissue, the connector is retained in the pre-installed longitudinal shape by a connector alignment module. In various embodiments, the outer plate is a first outer plate of a plurality of outer plates and the connector is a first connector of a plurality of connectors, wherein the method further comprises engaging the plurality of outer plates against the cardiovascular tissue and interconnecting the connection interface to the plurality of outer plates, respectively, using the plurality of connectors, respectively. In various embodiments, the connector alignment module includes a plurality of chambers for respectively housing the plurality of connectors in the pre-installed longitudinal shape. In various embodiments, approximating the first outer plate relative to the connection interface comprises coupling an implantation tool to the connector alignment module and actuating a first actuating mechanism of the implantation tool. In various embodiments, inserting the first connector through the cardiovascular tissue includes actuating a second mechanism of the implantation tool to deploy the first connector from a respective chamber of the plurality of chambers of the connector alignment module. The method may further include successively deploying the plurality of connectors from the plurality of chambers of the connector alignment module.

In various embodiments, the method includes tensioning the connector. The method may include, after engaging the distal end of the connector to the receptacle of the outer plate, at least one of capping, crimping, and cutting the distal end of the connector. In various embodiments, interconnecting the connection interface to the outer plate using the connector includes extending the connector outside of the cardiovascular tissue. In various embodiments, the connector comprises a connection tab extending from the connection interface, the outer plate comprises a ratcheting mechanism, and interconnecting the connection interface to the outer plate using the connector comprises engaging a portion of the connection tab to the ratcheting mechanism.

Also disclosed herein, according to various embodiments, is a ventricular assist system. The ventricular assist system may include an implantable anastomotic assembly that is configured to be attached to a ventricle. The implantable anastomotic assembly may include a connection interface, a plurality of outer plates, and a plurality of connectors configured to extend between and interconnect the connection interface and the plurality of outer plates, respectively. Each outer plate of the plurality of outer plates may be configured to be engaged against the ventricle before a respective connector of the plurality of connectors is interconnected between the connection interface and each outer plate of the plurality of outer plates. The ventricular assist system may also include a connector alignment module configured to hold the plurality of connectors in a pre-installed longitudinal shape and an implantation tool configured to successively approximate the plurality of outer plates relative to the connection interface and successively deploy the plurality of connectors. In various embodiments, the connection interface includes a support ring, wherein the ventricular assist system further comprises an assembly tool configured to facilitate coupling the support ring to an apical cuff.

The forgoing features and elements may be combined in various combinations without exclusivity, unless otherwise expressly indicated herein. These features and elements, as well as the operation of the disclosed embodiments, will become more apparent in light of the following description and accompanying drawings.

BRIEF DESCRIPTION OF THE DRAWINGS

FIG. 7A is a perspective view of a step of a method of engaging a connection interface of an implantable anastomotic assembly to an apical cuff, in accordance with various embodiments;

FIG. 7B is a perspective view of another step of a method of engaging a connection interface of an implantable anastomotic assembly to an apical cuff, in accordance with various embodiments;

Figure 1A:
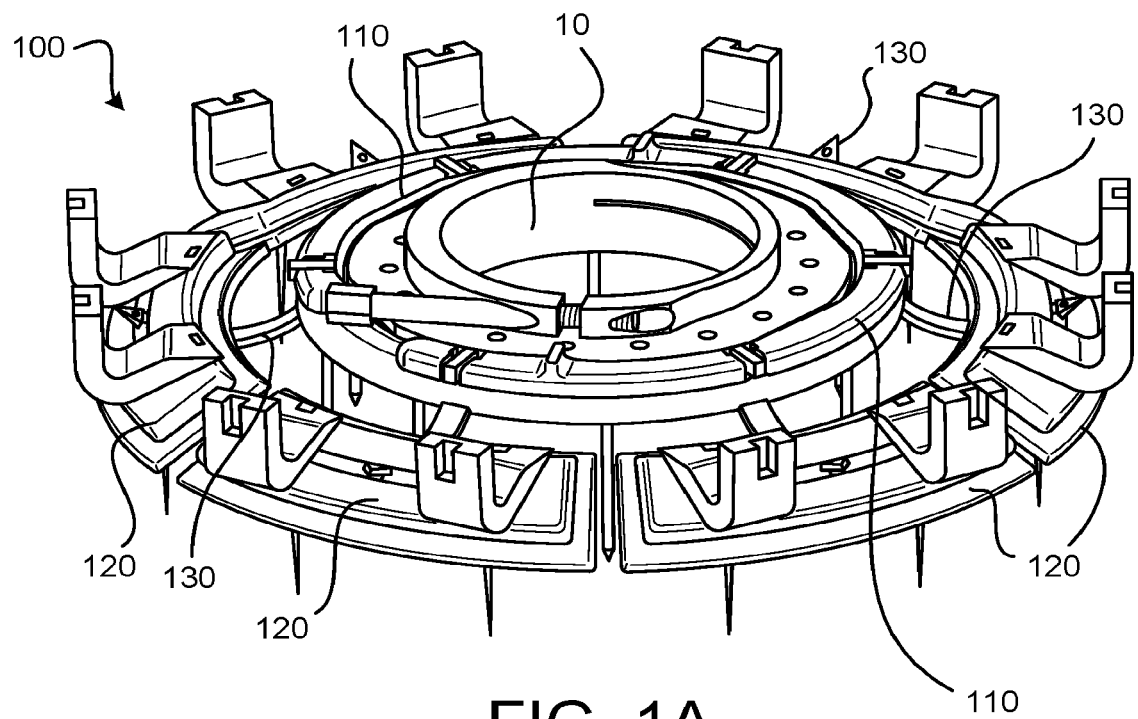
FIG. 1A is a perspective view of an implantable anastomotic assembly that is configured to be attached to cardiovascular tissue, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration. Although these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and is not limiting.

Figure 1B:
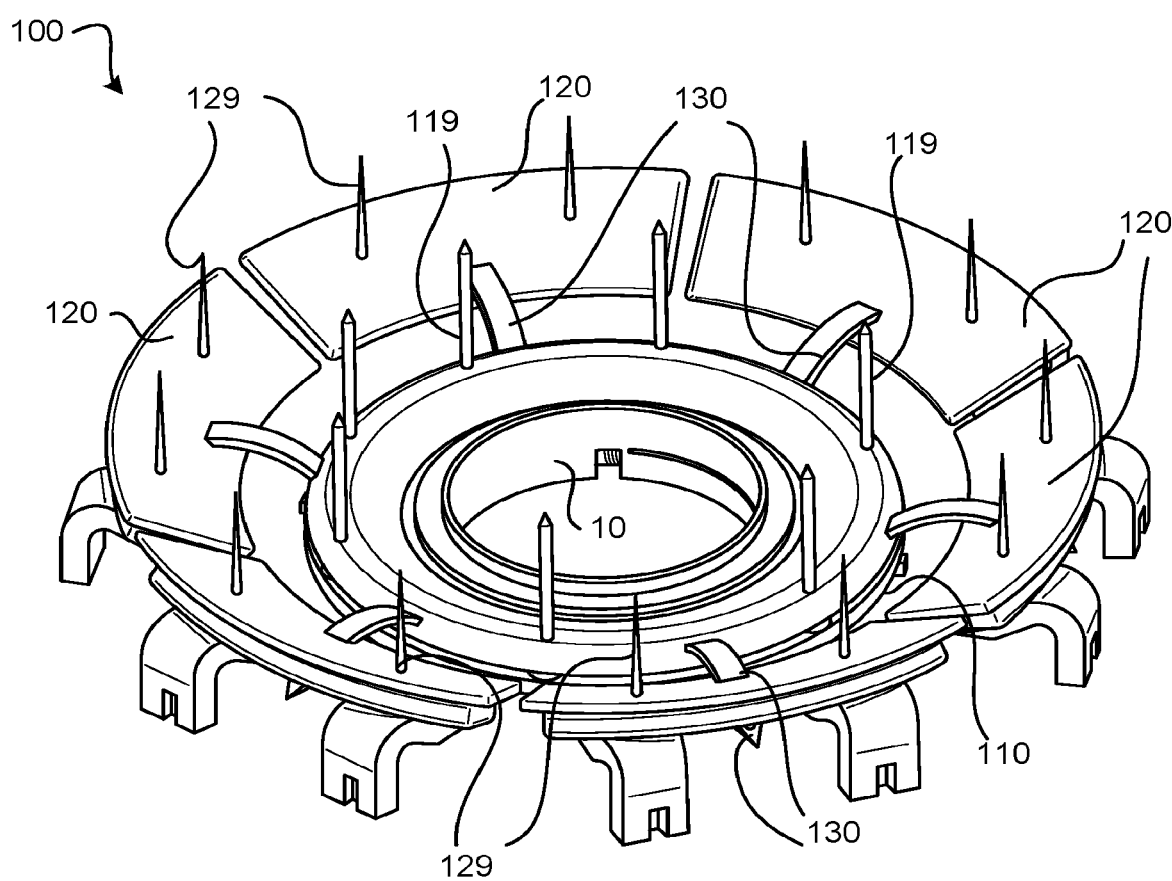
FIG. 1B is another perspective view of an implantable anastomotic assembly that shows surfaces of the assembly that are configured to face and engage the cardiovascular tissue, in accordance with various embodiments.
Figure 1C:
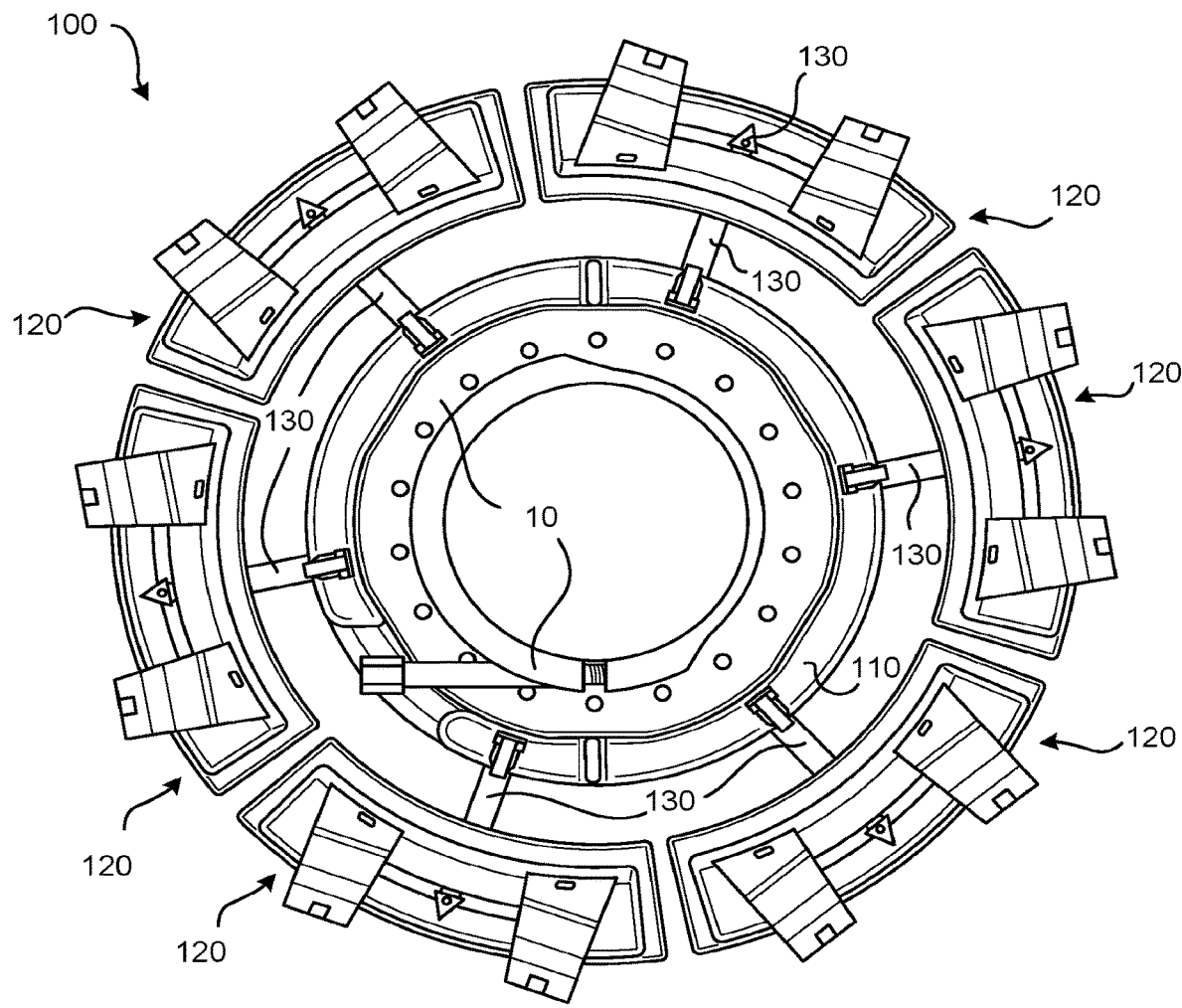
FIG. 1C is a plan view of an implantable anastomotic assembly, in accordance with various embodiments.

In various embodiments and with reference to FIGS. 1A, 1B, and 1C, an implantable anastomotic assembly 100 is provided. The implantable anastomotic assembly 100 is configured to enable a practitioner to quickly and easily attach a connection interface to cardiovascular tissue of a patient, according to various embodiments. As used herein, the term "anastomotic" generally refers to surgical openings and/or connections formed in cardiovascular tissue. For example, the implantable anastomotic assembly may be utilized to facilitate surgical installation of a ventricular assist device ("VAD") in a patient, according to various embodiments. As described in greater detail below, the disclosed assembly 100, and the associated tools and methods, provide various benefits over conventional VAD installation techniques, including decreased surgical times (e.g., reducing or perhaps even eliminating the time the patient is on cardiopulmonary bypass), increased ease and reproducibility of installation, a decrease in bleeding, and a decrease in costs, according to various embodiments. In various embodiments, the implantable anastomotic assembly 100, in conjunction with the associated tools and implantation steps described below, is not necessarily intended to eliminate the use of cardiopulmonary bypass for VAD installation procedures, though certain surgeons may choose to attempt off-bypass implantation using these disclosed concepts. Generally, the present disclosure provides for placement of an apical cuff prior to coring the ventricular tissue at the site of cuff implantation, according to various embodiments. Accordingly, the present disclosure may enable LVAD installation by full sternotomy and/or limited left thoracotomy approaches.

Although numerous details and embodiments are provided herein pertaining to the use of the implantable anastomotic assembly 100 and its associated tools and methods for VAD installation (e.g., installation of an LVAD apical cuff onto the heart of a patient), the principles disclosed herein may be applied to other surgical procedures and applications. That is, the provided disclosure generally relates to one or more methods, devices, and systems for attaching a connection interface (e.g., an apical cuff/sewing ring) to cardiovascular tissue of a patient, and is not necessarily limited to LVAD installation applications.

Figure 12:
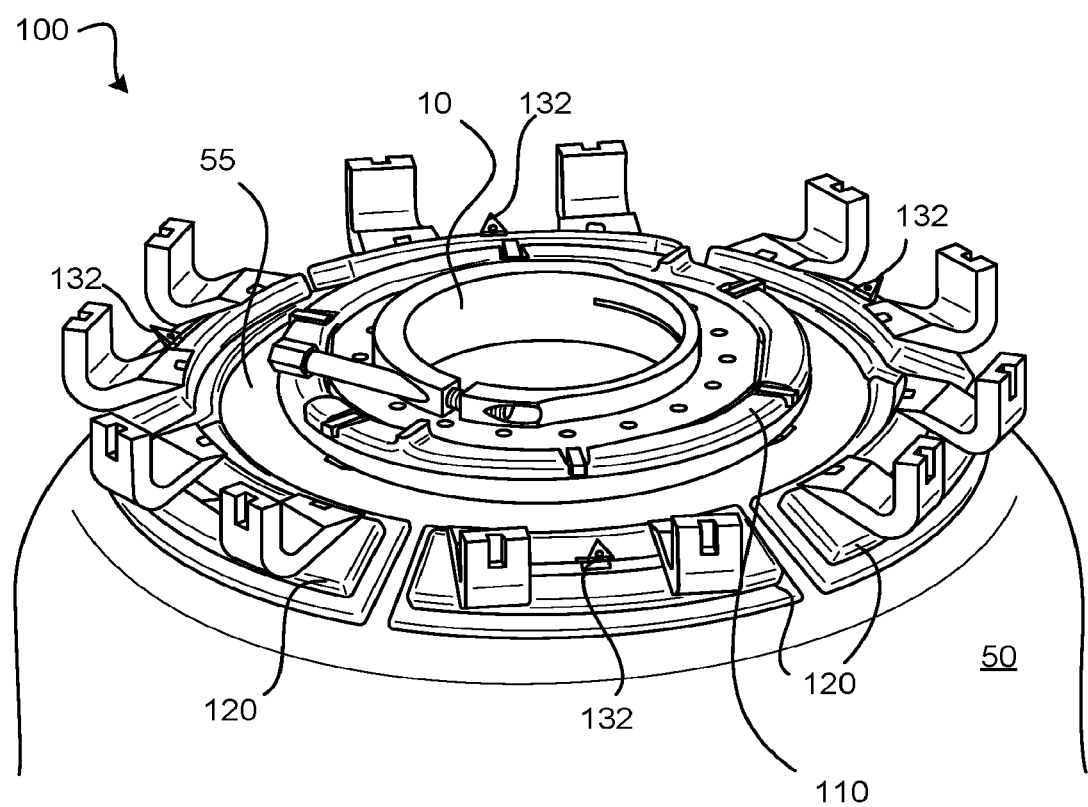
FIG. 12 is a perspective view of an implantable anastomotic assembly attached/implanted/installed on a ventricle in accordance with various embodiments.

Generally, the implantable anastomotic assembly includes a connection interface 110, a plurality of outer plates 120, and a plurality of connectors 130 that are configured to extend between and interconnect the connection interface 110 and the plurality of outer plates 120. The term "connection interface" 110 refers generally to a component that is being coupled/grafted to cardiovascular tissue around a stoma or other opening formed in the cardiovascular tissue. Accordingly, the term "connection interface" 110 may refer to a support ring that is coupled to an existing apical cuff of a conventional VAD (e.g., the cuff 10 shown in the figures), or the term "connection interface" may refer to a modified apical cuff. That is, the term "connection interface," though often used herein to refer to the support ring that is coupled to a conventional apical cuff, may instead refer to an apical cuff that has the functionality/features of the retrofit combination of a conventional apical cuff with a support ring connected thereto. Accordingly, the connection interface may be utilized as an attachment point for other components, such as a pump for use in a VAD application. Accordingly, and with specific momentary reference to FIG. 1B, the connection interface 110 may include tines 119 and the plurality of outer plates 120 may include tines 129 that pierce the cardiovascular tissue to facilitate retention of the respective components. For example, and with reference to FIG. 12, the implantable anastomotic assembly 100 may be attached to a heart 50 and may be configured to form a hemostatic gasket 55 of myocardium between the connection interface 110 and the plurality of outer plates 120, with the plurality of connectors 130 extending between and interconnecting the connection interface 110 and the plurality of outer plates 120, as described in greater detail below.

Figure 14A:
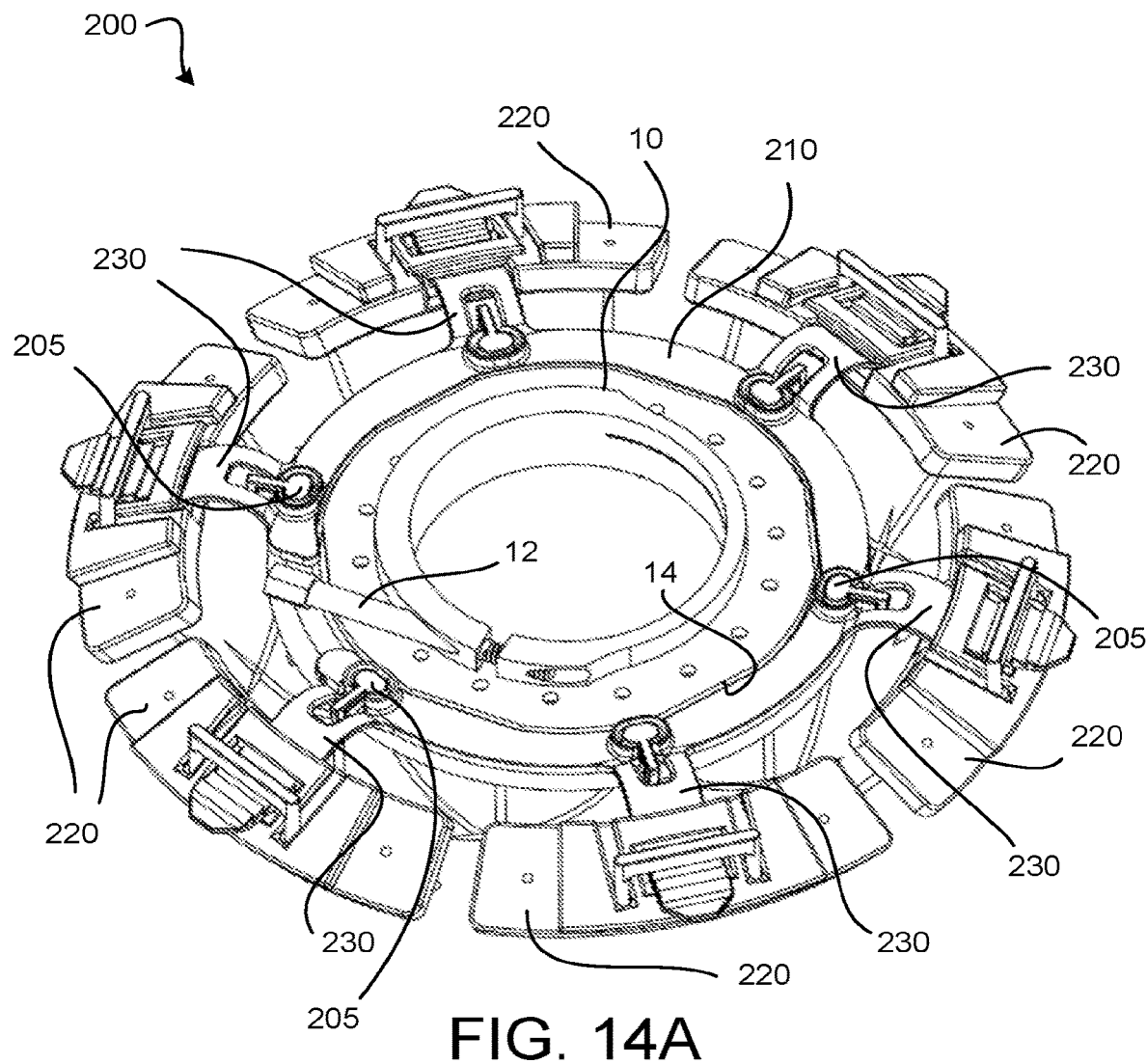
FIG. 14A is a perspective view of another implementation of an implantable anastomotic assembly, in accordance with various embodiments.
Figure 14B:
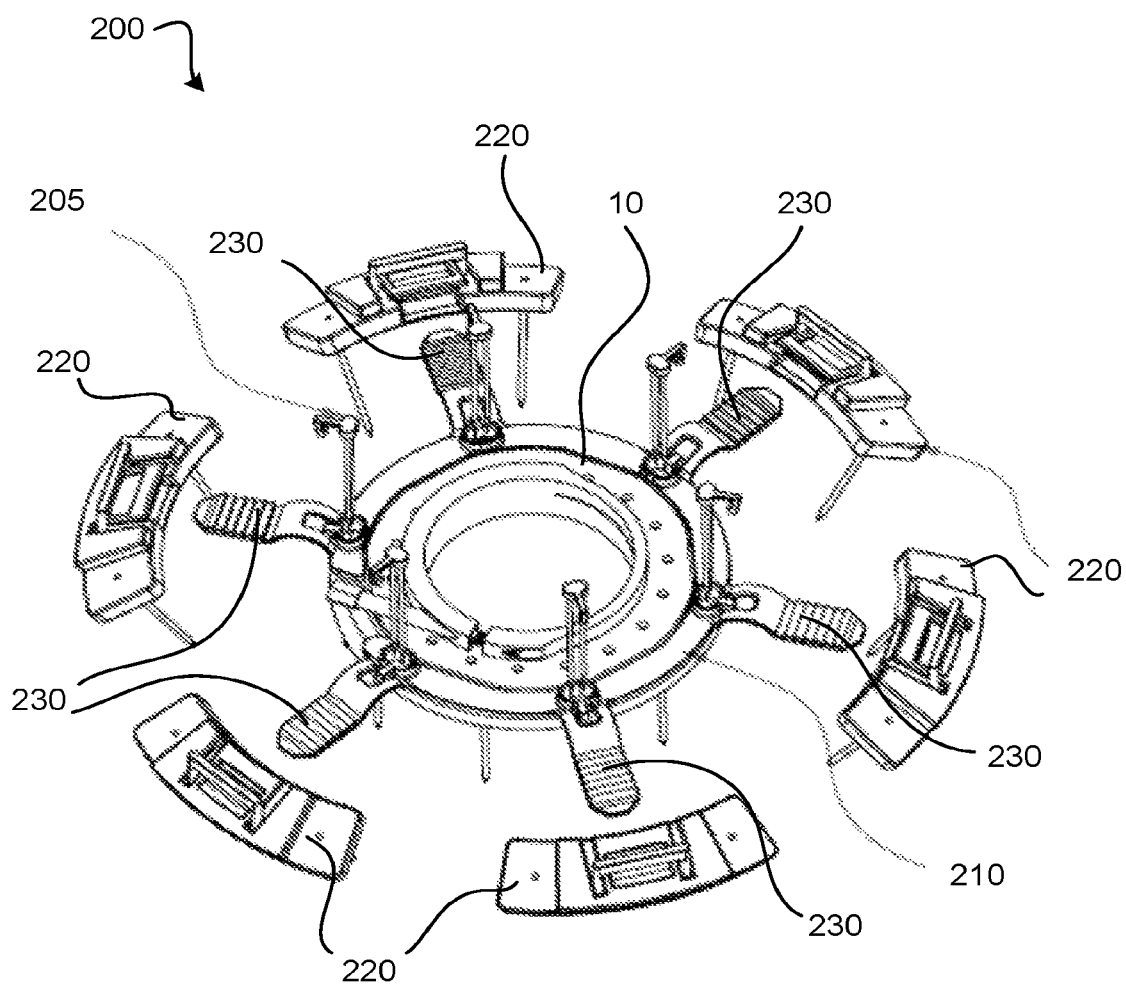
FIG. 14B is an exploded perspective view of another implementation of an implantable anastomotic assembly, in accordance with various embodiments.

In various embodiments, and again with reference to FIGS. 1A, 1B, and 1C, the connection interface 110 is separate from the plurality of outer plates 120 before implantation such that the connection interface 110 may only be connected to the plurality of outer plates 120 after an outer plate of the plurality of outer plates 120 is engaged against cardiovascular tissue. Said differently, a first outer plate of the plurality of outer plates 120 is configured to be first engaged against the cardiovascular tissue before a respective connector of the plurality of connectors 130 is interconnected between the connection interface 110 and the first outer plate, according to various embodiments. According to various embodiments, FIGS. 14A and 14B show an additional, alternative implementation of the implantable anastomotic assembly, with like numerals denoting like components. That is, the implantable anastomotic assembly 200 of FIGS. 14A and 14B includes a connection interface 210, a plurality of outer plates 220, and a plurality of connectors 230. Additional details pertaining to this implementation of the implantable anastomotic assembly 200 are included below with reference to FIGS. 14A and 14B.

The remainder of the detailed description of this disclosure is outlined in this paragraph. Additional details pertaining to the implanted components/features of the implantable anastomotic assembly 100 are provided with reference to FIGS. 1A, 1B, 1C, 2, 3, 4A, 4B, 5A, and 5B. Additional details pertaining to the implanted components/features of the implantable anastomotic assembly 200 are provided with reference to FIGS. 14A, 14B, 15, 17, and 18. A method of using (e.g., a method of attaching/connecting/implanting) the implantable anastomotic assembly 100/200 is introduced and summarized with reference to FIG. 6. Assembly and delivery tools, as well as illustrative examples of steps of the method of implanting/attaching the implantable anastomotic assembly 100/200, are provided with reference to FIGS. 7A, 7B, 7C, 7D, 7E, 7F, 7G, 7H, 8, 9A, 9B, 9C, 9D, 10A, 10B, 11A, 11B, 11C, 11D, 11E, 11F, 12, 16A, and 16B. The various assembly and delivery tools shown and described with reference to FIGS. 7A, 7B, 7C, 7D, 7E, 7F, 7G, 7H, 8, 9A, 9B, 9C, 9D, 10A, 10B, 11A, 11B, 11C, 11D, 11E, 11F, 12, 16A, and 16B, such as apical cuff press 140, connection interface press 150, connector alignment module 160, preliminary connector positioning tool 170, and implantation tool 180, may be single-use (disposable) tools or may be reusable.

Figure 2:
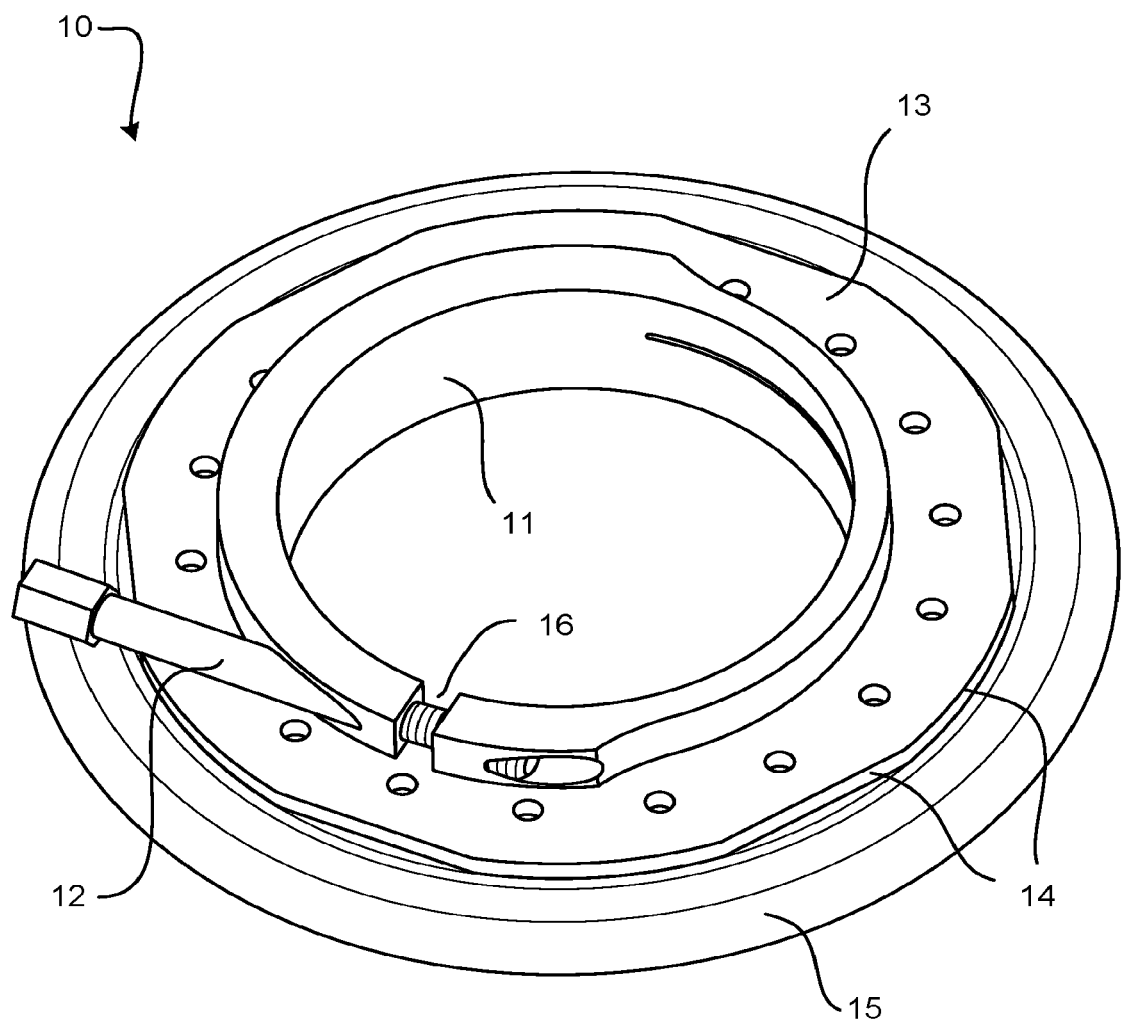
FIG. 2 is a perspective view of an apical cuff, in accordance with various embodiments.

In various embodiments, and with reference to FIG. 2, an apical cuff 10 of a VAD is provided. The connection interface 110, as described in greater detail below, may be coupled to an existing apical cuff, such as apical cuff 10. The apical cuff 10 may be, for example, a component of a Medtronic HVAD system that includes a tightening screw 12 configured to compress an inner bore 11 for attaching a pump thereto. In various embodiments, the apical cuff 10 may include a flange 13 that has an outer edge 14 with a specific shape. Further, the apical cuff 10 may include a sewing ring 15 configured to face the apex of the heart and to engage the outer surface of the myocardium. Although numerous figures included herein show this version of the apical cuff 10, the scope of the present disclosure is not limited to the depicted version of the apical cuff 10. That is, the apical cuff 10 may have a different structure or may have different features. For example, the apical cuff may be a component of the Abbott HeartMate 3', or other similar VAD kits.

Figure 3:
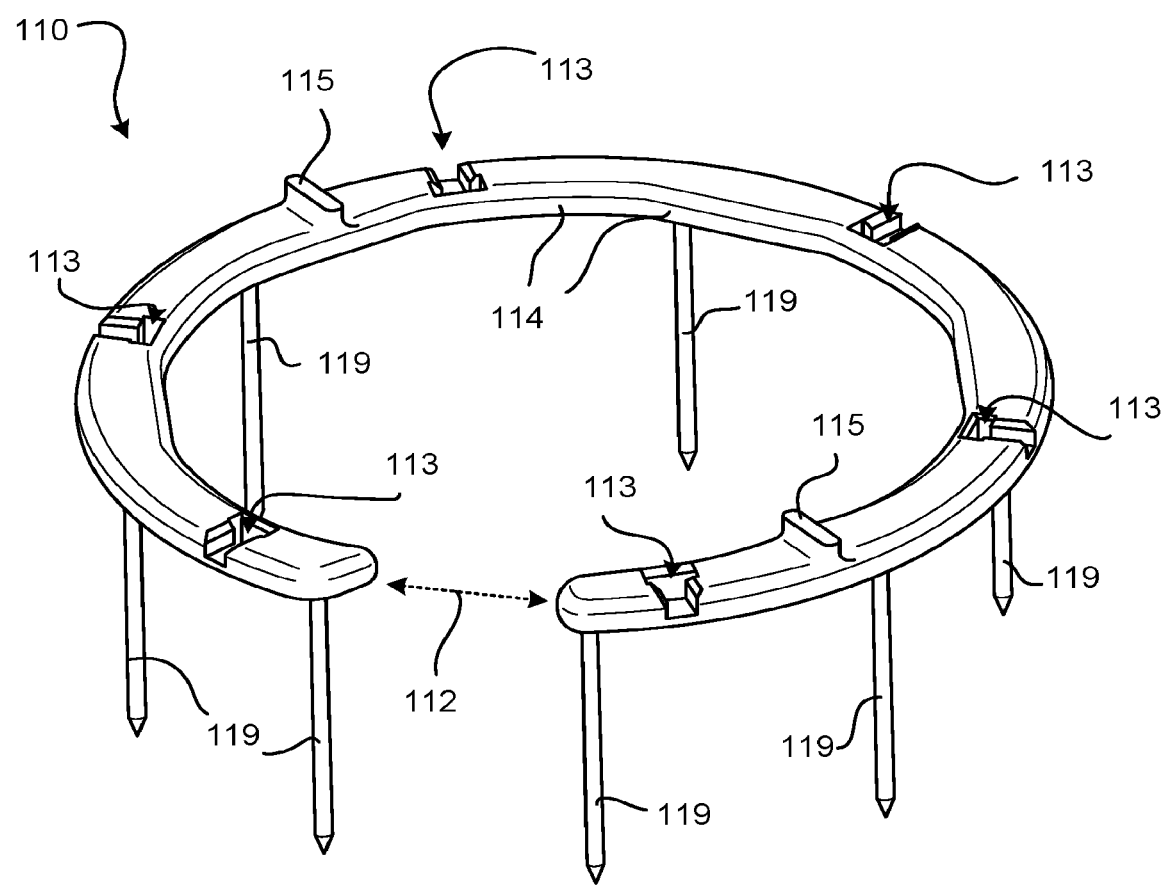
FIG. 3 is a perspective view of a support ring of a connection interface of an implantable anastomotic assembly, in accordance with various embodiments.

In various embodiments, and with reference to FIG. 3, the connection interface 110 is provided. The connection interface, as mentioned above, generally refers to the component that is being coupled/grafted to cardiovascular tissue around a stoma (already formed or to be formed) in the cardiovascular tissue. Although the connection interface 110 is repeatedly shown and described herein as being attachable to an apical cuff 10, the connection interface of the implantable anastomotic assembly 100 may be a single product that incorporates the functionality/features of both the connection interface 110 and the apical cuff 10 shown in the figures. The connection interface 110 may be referred to as a support ring, and may be configured to engage the apical cuff 10. The connection interface 110 may be a single, unitary component, or the connection interface may be comprised of multiple arcuate segments. The connection interface may have a continuous ring structure, or the connection interface 110 may be a partial ring in that a gap 112 is defined between ends of the ring structure. The gap 112, according to various embodiments, may be used to align the connection interface 110 with one or more features of the apical cuff. For example, the gap 112 may accommodate the tightening screw 12 of the apical cuff 10.

The connection interface 110 may be made from a metallic material. The connection interface 110 may have a surface 114 that is configured to complement a corresponding surface (e.g., edge 14) of the apical cuff to further promote secure engagement between the apical cuff 10 and the connection interface 110. In various embodiments, the connection interface 110 defines a plurality of apertures 113. The plurality of apertures 113 may be circumferentially distributed around the connection interface 110, and the plurality of connectors 130 may be at least partially inserted respectively through the apertures 113. As described in greater detail below, a top opening of each aperture of the plurality of apertures 113 may have a specific shape that is selected so as to be a retention seat for a tab of a connector of the plurality of connectors 130, as described in greater detail below.

The connection interface 110 may comprise a plurality of tines 119 that extend from a bottom surface of the connection interface 110, with the tines being configured to facilitate retention of the connection interface 110 and to help distribute force after the connection interface 110 is installed against the cardiovascular tissue. The connection interface 110 may also include one or more alignment features 115 that are used to facilitate alignment of the connection interface 110 during pre-implantation assembly, as described in greater detail below. The number of apertures 113 and the number of tines 119 is not limited to the number shown in the figures. That is, the number of apertures 113 and tines 119 may be selected according to the specifics of a given application.

Figure 4A:
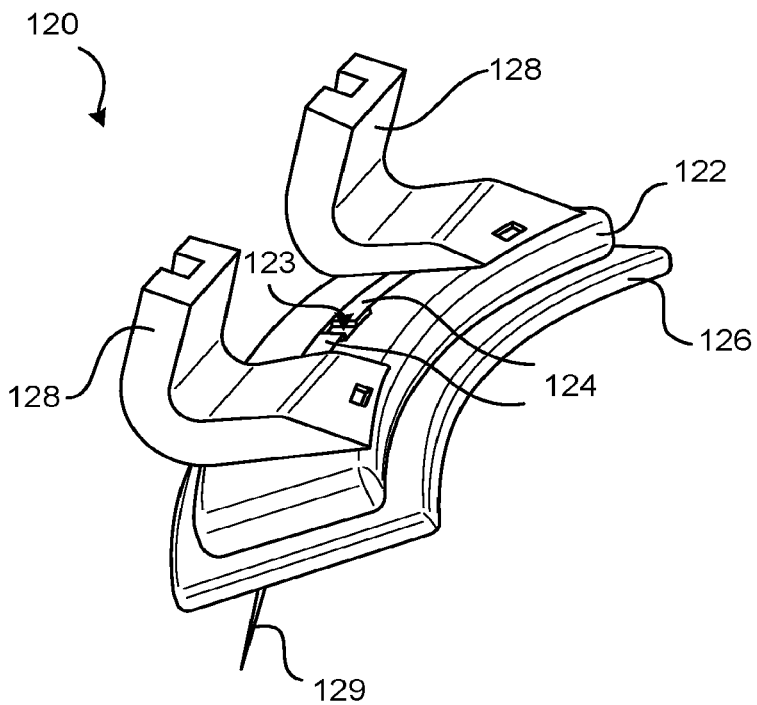
FIG. 4A is a perspective view of an outer plate of an implantable anastomotic assembly, in accordance with various embodiments.
Figure 4B:
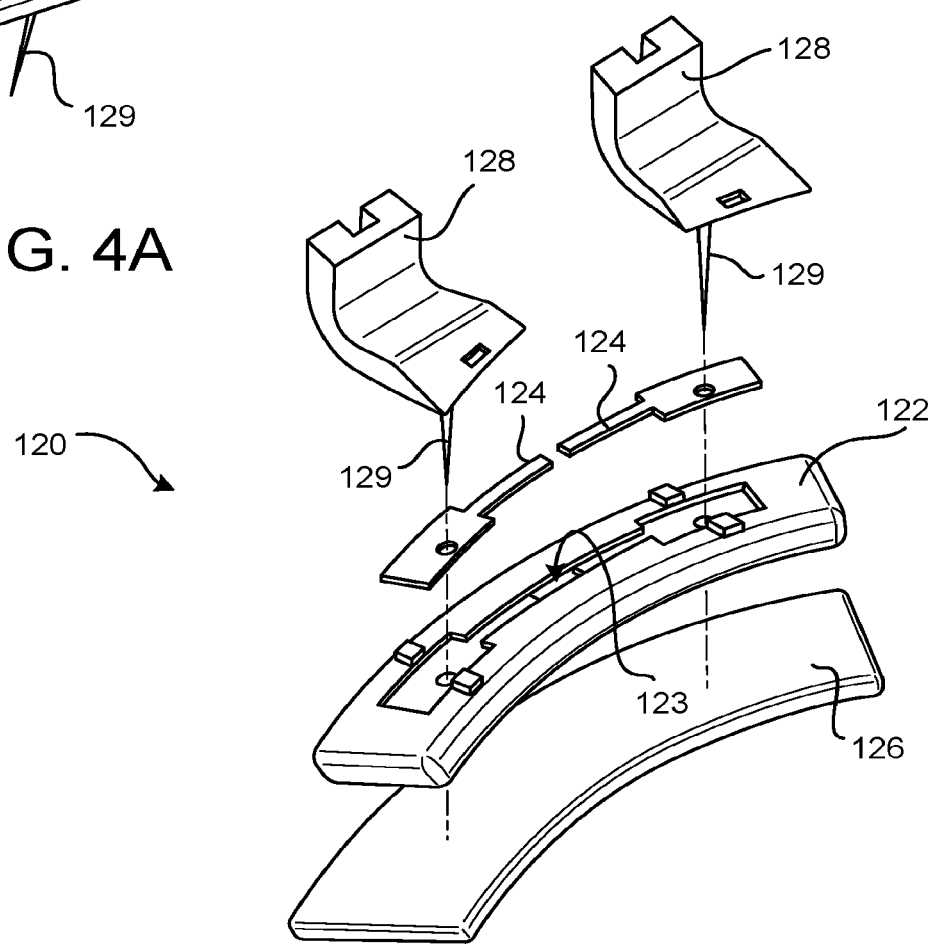
FIG. 4B is an exploded perspective view of an outer plate of an implantable anastomotic assembly, in accordance with various embodiments.

In various embodiments, and with reference to FIGS. 4A and 4B, one outer plate of the plurality of outer plates 120 is provided. Although the number of outer plates 120 (and connectors 130 for that matter) shown in the figures (e.g., FIGS. 1A, 1B, and 1C) is six, the present disclosure is not limited to six, and thus the implantable anastomotic assembly 100 may have more or less. For example, in various embodiments the implantable anastomotic assembly may have two or more outer plates (with a corresponding number of connectors, or with multiple connectors for each outer plate). In various embodiments, the implantable anastomotic assembly may include a single, ring-like outer plate. In various embodiments, each outer plate 120 comprises a body 122. The body 122 may be curved in two directions. That is, the body 122 of each outer plate 120 may form an arcuate segment of a ring shape that extends around, and is generally concentric with, the connection interface 110 in response to the implantable anastomotic assembly 100 being in the installed position (see FIG. 12). The body 122 of each outer plate 120 may also have a bottom surface that is concave, thereby conforming to the epicardial surface of myocardium of the ventricle. In various embodiments, the bottom surface (e.g., the concave bottom surface) may have a buttress material 126, such as a felt or polytetrafluoroethene, which helps to prevent tearing of the epicardium and to improve hemostasis between the outer plate 120 and the epicardium.

In various embodiments, each outer plate 120 may include one or more tines 129 that extend from the bottom surface of the outer plate 120 and impale the epicardial surface and embed in the myocardium. The purpose of the tines 129 is to equalize the distribution of central compressive forces that push the intervening myocardium against the apical cuff to achieve hemostasis. These tines 129 may be integrated into grasping elements 128, as shown in FIG. 4B. In various embodiments, each outer plate 120 may include one or more grasping elements 128 that are used to facilitate radially inward approximation of the outer plate 120 toward the connection interface 110/apical cuff 10. While this concept is described in greater detail below, the grasping element(s) 128 may be grasped by a practitioner, either directly or via an implantation tool, such as implantation tool 180 described below with reference to FIGS. 10A, 10B, 11C, 11C, and 11E, to facilitate translation of each outer plate 120 toward the connection interface 110 to create the myocardial gasket 55 (FIGS. 11E and 12) between the connection interface 110 and the plurality of outer plates 120. In various embodiments, the grasping element 128 may have outside notches that are attachable to the implantation tool 180. The tines 129, according to various embodiments, may extend from the bottom of grasping element(s) 128 and may extend through holes/windows in the body 122 of the outer plate 120.

In various embodiments, each outer plate 120 defines a receptacle 123. The receptacle 123 is generally configured to receive a portion of a connector of the plurality of connectors, according to various embodiments. For example, each connector of the plurality of connectors 130 may be configured to be inserted through a respective aperture of the plurality of apertures 113 defined in the connection interface 110 and to engage with the receptacle 123 of a respective outer plate 120. In various embodiments, each outer plate 120 is configured to be coupled to a single connector 130. In various embodiments, each outer plate 120 defines a single receptacle 123 positioned in the center of the outer plate 120. The receptacle 123 may be a window that has a larger opening on the bottom side than on the top side. The bottom opening of the receptacle 123 may also have beveled/chamfered edges to facilitate reception of a distal end of a respective connector within the receptacle 123. In various embodiments, one or more resiliently flexible tabs 124 may extend partially across the top opening of the receptacle 123. The one or more resiliently flexible tabs 124 may be configured to flex in an upward direction in response to the distal end of the connector being inserted there through. As described in greater detail below with reference to FIGS. 5A and 5B, notches defined adjacent the distal end of the connector are configured to engage the resiliently flexible tabs 124 to prevent the connector from being extracted back out from the receptacle, and thus facilitate retention of the connector relative to the outer plate 120. The resiliently flexible tabs 124 may be made from a spring steel material, for example. In various embodiments, the resilient flexible tabs 124 comprise an embedded portion that is disposed between the grasping elements 128 and the body 122 of the outer plate 120. In various embodiments, the embedded portion also has a hole through which the tine 129 may extend.

Figure 5A:
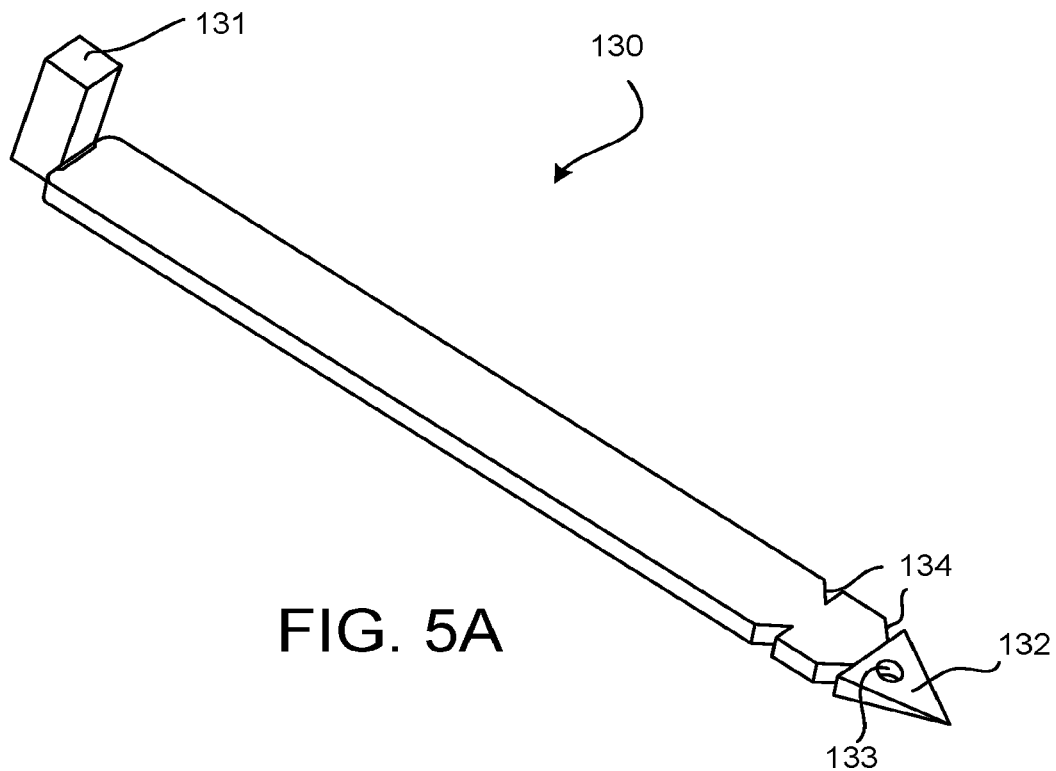
FIG. 5A is a perspective view of a connector of an implantable anastomotic assembly having a pre-installed longitudinal shape, in accordance with various embodiments.
Figure 5B:
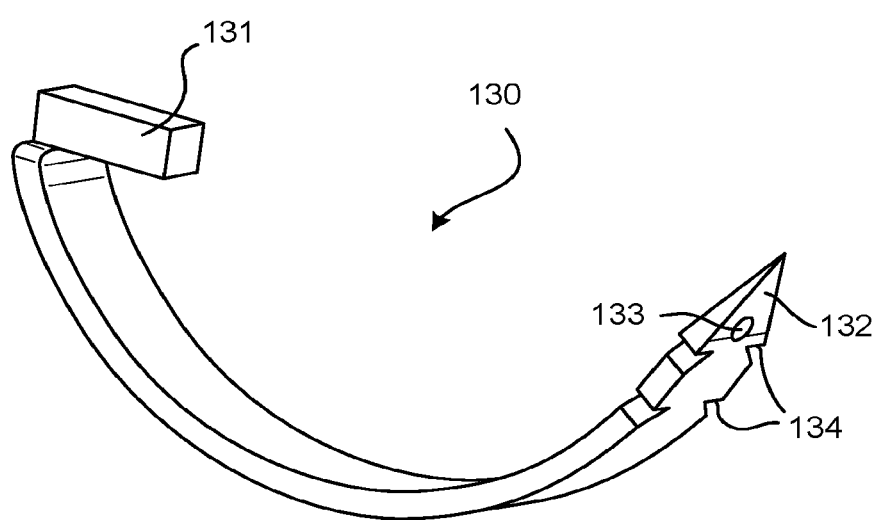
FIG. 5B is a perspective view of a connector of an implantable anastomotic assembly having an installed longitudinal shape, in accordance with various embodiments.

In various embodiments, and with reference to FIGS. 5A and 5B, individual connectors of the plurality of connectors 130 are provided. The connectors 130 are generally configured to extend between and interconnect the connection interface 110 with the plurality of outer plates 120. In various embodiments, the connectors 130 may be sutures, tissue anchors, wires, or other forms of elongate members. The connectors 130 may have a fixed shape, or the connectors 130 may be made from a shape memory material, such as nitinol, beta titanium, or other medical grade material with superelastic and/or shape memory properties. For example, in various embodiments, connector 130 may be formed from nitinol, an intermetallic compound having approximately 50.8 atomic percent nickel and the balance titanium. Nitinol has the unique properties of shape memory and superelasticity, and may be able to withstand unusually high levels of strain (up to 8% or more), without experiencing plastic deformation. The material can have an unusually pronounced hysteresis effect in its stress-strain relationship. That is, in response to a load, stresses are relatively high as they reach the upper plateau (UP) where a phase change from austenite to martensite occurs. In response to removing the load, stresses are relatively low, as seen in the lower plateau (LP) where the material transforms from martensite to austenite. The magnitude of the difference between UP and LP stresses is determined by material composition, as well as thermal and processing history. In various embodiments, the transition temperature for the material, known as the Austenite Finish (Af) temperature is preferably set between 10 degrees and 37 degrees C. In various embodiments, the recovery from the elongate form to the curved form in response to deployment is controlled by the LP stress. Therefore thermal processing may be preferentially selected to achieve a desired Af temperature and LP stress that is suitable for the connector 130 to traverse the cardiovascular tissue, and consistently emerge at a desired location such that distal tip 132 can be reliably captured by the outer plate(s).

In various embodiments, connector 130 may be described as having a wall thickness T (the substantially vertical direction of perspective view 5A), a width W (the substantially horizontal direction of perspective view 5A), an elongate length L (generally the distance from 131 to 132 of 5A), and formed radius of curvature R (the curvature depicted in 5B). In various embodiments, the maximum surface strains resulting from straightening from the curved form of FIG. 5B to the elongate form of FIG. 5A can be approximated by T/2R. In various embodiments, the connector 130 may be capable of transforming from the curved form to the elongate form, and may be capable of subsequently returning to the curved form upon deployment, without experiencing plastic deformation. Accordingly, to remain within typical limits of nitinol superelasticy, the T/2R ratio may be less than or equal to approximately 0.08, corresponding to 8% strain, according to various embodiments. It is understood that notches or other features, such as 132 or 134 tend to concentrate stress and locally elevate strain, such that this 8% strain guidance may be exceeded without substantially degrading the functional performance of the component.

Figure 8:
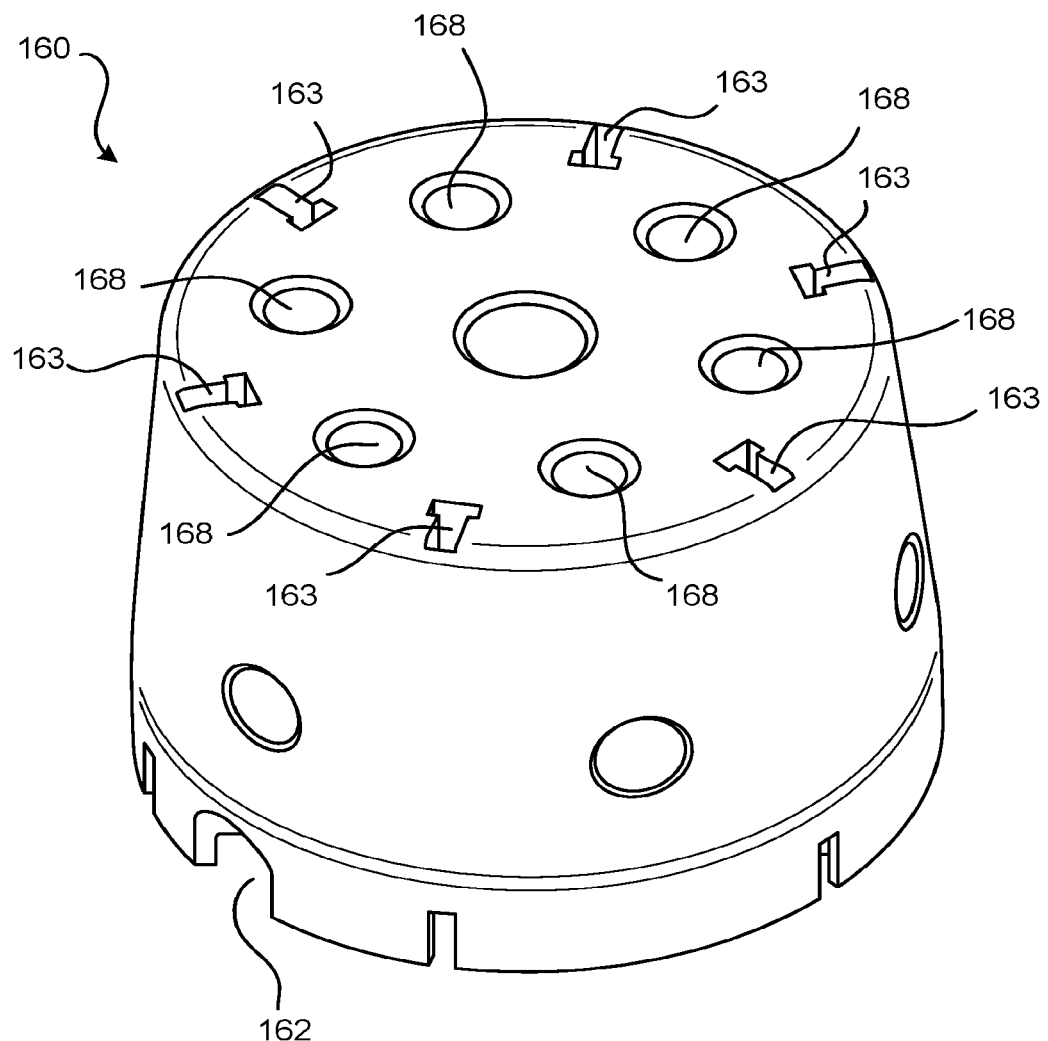
FIG. 8 is a perspective view of a connector alignment module, in accordance with various embodiments.

In various embodiments, the connectors 130 may be configured to assume a specific shape/orientation in response to deployment of the connectors 130. For example, the connectors 130 may be configured to automatically transition from a pre-installed longitudinal shape (e.g., linear, FIG. 5A) to an installed longitudinal shape (e.g., non-linear, curved, FIG. 5B) after they are inserted through the cardiovascular tissue. In various embodiments, the connectors 130 may be pre-installed in a connector alignment module 160 (FIG. 8). Accordingly, in response to being deployed from the connector alignment module 160, as described in greater detail below, the connectors 130 may automatically transition to their preferred, desired, i.e., "installed" longitudinal shape (e.g., the curved shape shown in FIG. 5B). In various embodiments, the connectors 130 may maintain a curved longitudinal shape after being installed. In various embodiments, the curvature of the connectors 130 once installed may be opposite the localized curvature of the myocardium. That is, the center(s) of curvature of each connector 130 in the installed longitudinal shape may be disposed in the myocardium or outside of the heart while the center(s) of curvature of the myocardium may be generally disposed within the ventricular chamber of the heart.

In various embodiments, as each connector 130 passes through a respective aperture of the plurality of apertures 113 of the connection interface 110, the connectors 130 begin to assume their installed (e.g., natural, pre-configured, pre-learned) longitudinal orientation/shape. The tendency of the connectors 130 to assume their programmed, desired longitudinal shape causes the connectors 130 to redirect within the myocardium and ultimately be routed/redirected such that the distal end 132 of each connector 130 engages a respective of the plurality of receptacles 123 of the outer plate 120. In various embodiments, the connectors 130 extend radially outward from the connection interface 110 through the myocardium toward the outer plates 120. Accordingly, although practitioner intervention may be needed to actuate deployment/injection of the connectors 130, the structure of the connectors 130 enables the insertion and routing of the connectors 130 to be performed automatically (i.e., without human intervention), according to various embodiments. In various embodiments, the connectors may be deployed from the outer plates and may extend radially inward toward the connection interface.

In various embodiments, the connectors 130 may have a non-circular cross-sectional shape (e.g., rectangular shape), which may facilitate directional control of the connectors 130 during deployment by being held/retained within the connector alignment module 160 in the proper orientation. In various embodiments, a proximal end 131 of the connectors 130 has a retention feature, such as a "T-shape" or a flat head that is configured to retain and secure the connector against the surface of the connection interface 110 adjacent the apertures 113. In various embodiments, a distal end 132 of each connector 130 may have a beveled edge or may otherwise have a sharp tip that facilitates movement of the connector through the myocardium. The distal end 132 of each connector 130 may have an engagement feature that interfaces with the respective receptacles 123 of the outer plate 120. In various embodiments, the engagement feature(s) at the distal end 132 of the connector 130 may automatically connect to the receptacle 123 defined by the outer plate 120. For example, one or more notches 134 may be defined at or adjacent the distal end 132 of the connector 130, and these notches 134 may engage the resiliently flexible tabs 124 of the outer plates 120, as described above. In various embodiments, the connectors may have more notches, or the notches may be configured to have different shapes/orientations. Further, the distal end 132 of each connector may have other features that facilitate coupling between respective connectors 130 and respective outer plate 120. In various embodiments, the distal end 132 of the connector 130 may have a hole 133 through which a cap or other retention feature may be inserted to secure the connection between the distal end 132 of the connector 130 and the outer plate 120. In various embodiments, the assembly 100 eliminates the need for manual knot tying, as is customary for conventional LVAD installations.

In various embodiments, the coupling between the distal end of each connector and a respective outer plate may be achieved via other means. For example, a cam mechanism, friction mechanism, a spring-loaded engagement mechanism, or other such mechanisms may be used to form the coupling. Further, after the distal end of the connector passes through the receptacle of the outer plate, the distal end of the connector may be further tensioned or may be cut, crimped, or otherwise secured to the outer plate. In various embodiments, tensioning the connector comprises pulling on either end of the connector 130 to increase the tension. However, the shape memory property of the connectors 130 may, in various embodiments, provide an appropriate degree of tension such that no manual tensioning is needed. In various embodiments, and with momentary reference to FIGS. 13A and 13B, a cap 135 may be disposed around the distal end 132 of the connector 130, and the cap 135 may be crimped or otherwise deformed to prevent backward retraction of the distal end 132 of the connector 130 from engagement with the outer plate 120, and to cover the sharp tip of the distal end 132.

Figure 6:
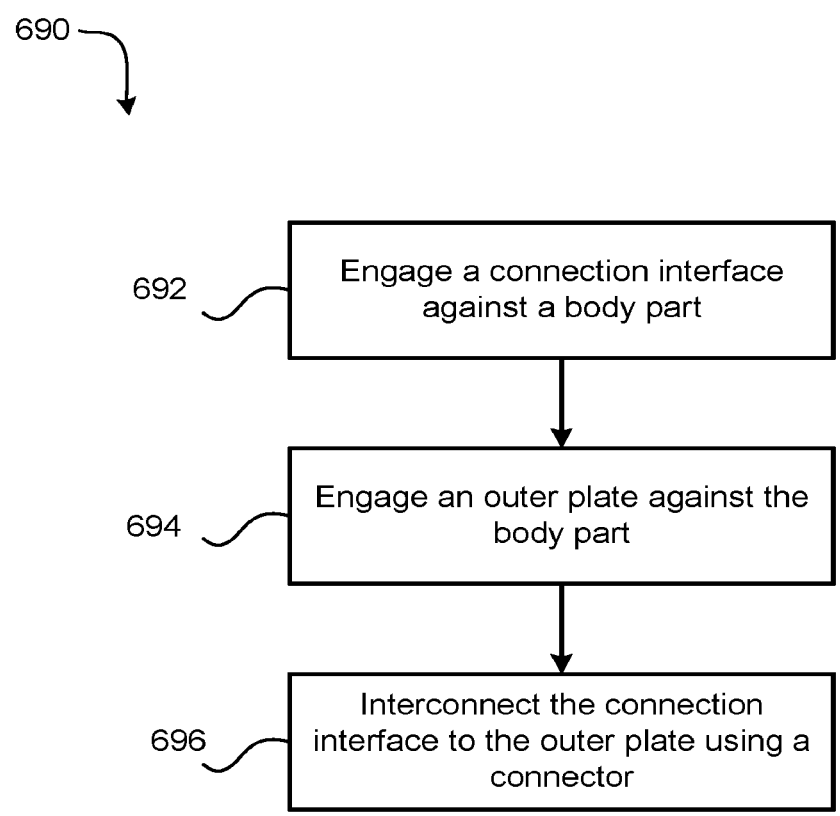
FIG. 6 is a schematic flow chart diagram of a method of attaching an implantable anastomotic assembly to cardiovascular tissue, in accordance with various embodiments.

In various embodiments, and with reference to FIG. 6, a method 690 of attaching an implantable anastomotic assembly 100 to cardiovascular tissue is provided. The method 690 may include, according to various embodiments, engaging a connection interface 110 against the cardiovascular tissue at step 692, engaging an outer plate against the cardiovascular tissue at step 694, and interconnecting the connection interface 110 to the outer plate 120 using a connector 130 at step 696. In various embodiments, step 696 is performed after step 692 and 694. Said differently, before step 696 of interconnecting the connection interface 110 and the outer plate 120 using the connector 130, the connection interface 110 may be separate from and non-contiguous with the outer plate 120.

Step 696 of interconnecting the connection interface to the outer plate may be performed via inserting connectors through cardiovascular tissue, such as through myocardium, or may be performed by extending the connector external to the cardiovascular tissue, such as external to the myocardium. In various embodiments, the method 690 may include an additional step of approximating the outer plate relative to the connection interface. This approximation step may be performed after steps 692 and 694. In various embodiments, this approximation step is also performed before step 696. As used herein, the term "approximating" generally refers to the concept of bringing components closer together.

In various embodiments, steps 692, 694, and 696 of the method 690 may be performed for each outer plate and each connector of the plurality of outer plates and the plurality of connectors, respectively. In various embodiments, each connector of the plurality of connectors may be connected to a respective outer plate of the plurality of outer plates individually, and the method 690 may include successively performing these steps for the remaining outer plates and associated connectors. In various embodiments, a first grouping of connectors (e.g., a pair of connectors) may be connected to a respective grouping of outer plates (e.g., a pair of outer plates) simultaneously, and the method 690 may include successively performing these steps on remaining groupings. By successively performing the steps of the method 690, the implantable anastomotic assembly may be installed via a thoracotomy, and may also enable the practitioner to accommodate variations in topographic anatomy. In various embodiments, all connectors may be connected to the outer plates simultaneously. These steps of the method 690, as well as various additional steps and/or auxiliary methods are described in greater detail below with reference to FIGS. 7A, 7B, 7C, 7D, 7E, 7F, 7G, 7H, 8, 9A, 9B, 9C, 9D, 10A, 10B, 11A, 11B, 11C, 11D, 11E, 11F, and 12.

In various embodiments, and with reference to FIGS. 7A, 7B, 7C, 7D, 7E, 7F, 7G, and 7H, various steps of a method/process for engaging the connection interface 110 to an apical cuff 10 are provided. For example, the method 690 of FIG. 6 may further include, before step 692 of engaging the connection interface 110 against the cardiovascular tissue, coupling the connection interface 110 (e.g., a support ring) to an apical cuff 10 of a ventricular assist device. In various embodiments, it may be important to properly align and seat the connection interface 110 relative to the apical cuff 10 before commencing the implantation surgery. Accordingly, the steps depicted in FIGS. 7A, 7B, 7C, 7D, 7E, 7F, 7G, and 7H may be performed on a back table in an operating room and/or by personnel assisting the practitioner/surgeon.

In various embodiments, and with specific reference to FIGS. 7A and 7B, an apical cuff press 140 is provided and the apical cuff 10 is seated on the apical cuff press 140. Alignment between the clocking key 144 and the apical cuff press 140 may be achieved via engagement of the body of the clocking key 144 itself within a corresponding feature, such as groove 147, of the apical cuff press 140. Alignment between the apical cuff 10 and the apical cuff press 140 may be achieved using a clocking key 144. For example, clocking key 144 may include a first alignment feature 146 that is configured to engage a corresponding feature 16 on the apical cuff. In other embodiments intended for other types of apical cuffs, the alignment features may differ or may not be necessary. Thus, engagement between the clocking key 144 itself and the slot 147 of the apical cuff press 140 as well as engagement between the first alignment feature 146 of the clocking key 144 and corresponding slot 16 of the apical cuff, the orientation of the apical cuff 10 seated against the apical cuff press 140 is known (via the clocking key 144). A handle 141 may be coupled to the opposing side of the apical cuff press 140. The apical cuff press 140 may include various other alignment features. In various embodiments, the apical cuff press 140 may define a plurality of tine slots 149, one or more second alignment features (e.g., bores 148), and one or more aperture alignment features 143. Generally, the tine slots 149 are configured to receive the tines 119 of the connection interface (described in greater detail below).

Figure 7D:
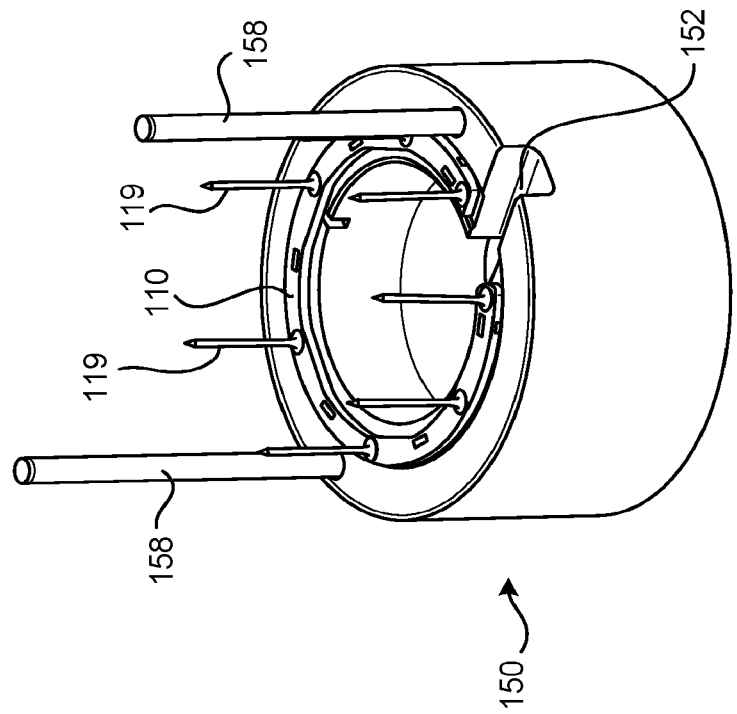
FIG. 7D is a perspective view of another step of a method of engaging a connection interface of an implantable anastomotic assembly to an apical cuff, in accordance with various embodiments.
Figure 7C:
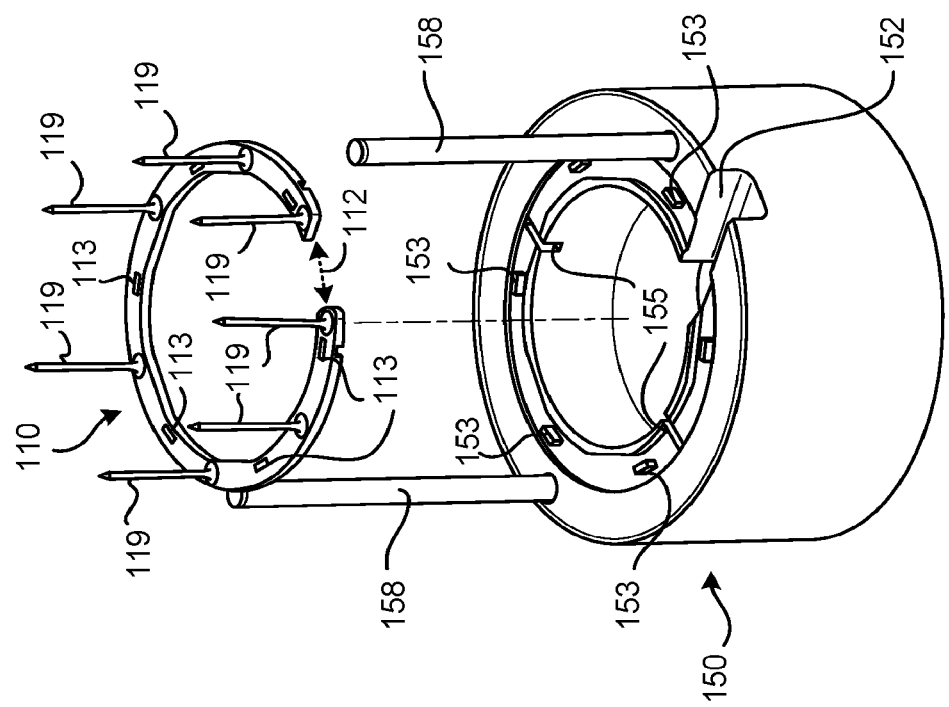
FIG. 7C is a perspective view of another step of a method of engaging a connection interface of an implantable anastomotic assembly to an apical cuff, in accordance with various embodiments.
Figure 7F:
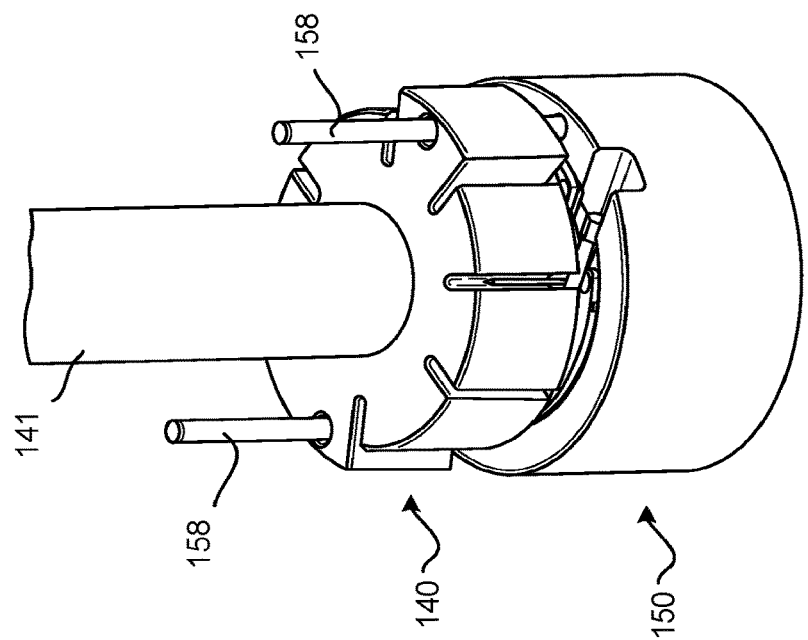
FIG. 7F is a perspective view of another step of a method of engaging a connection interface of an implantable anastomotic assembly to an apical cuff, in accordance with various embodiments.
Figure 7E:
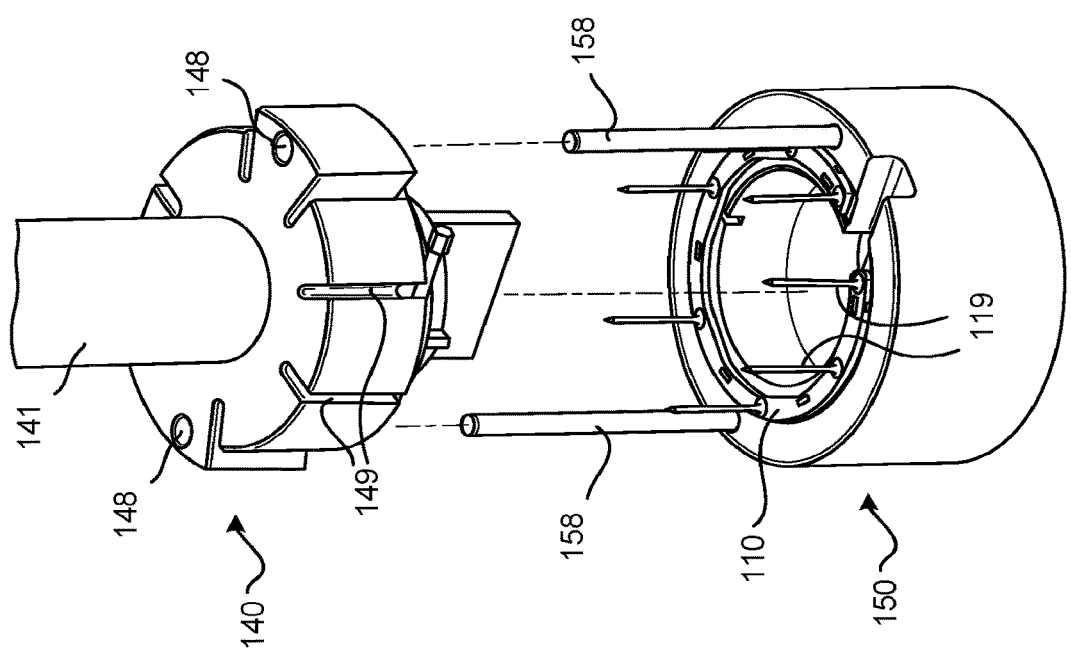
FIG. 7E is a perspective view of another step of a method of engaging a connection interface of an implantable anastomotic assembly to an apical cuff, in accordance with various embodiments.
Figure 7H:
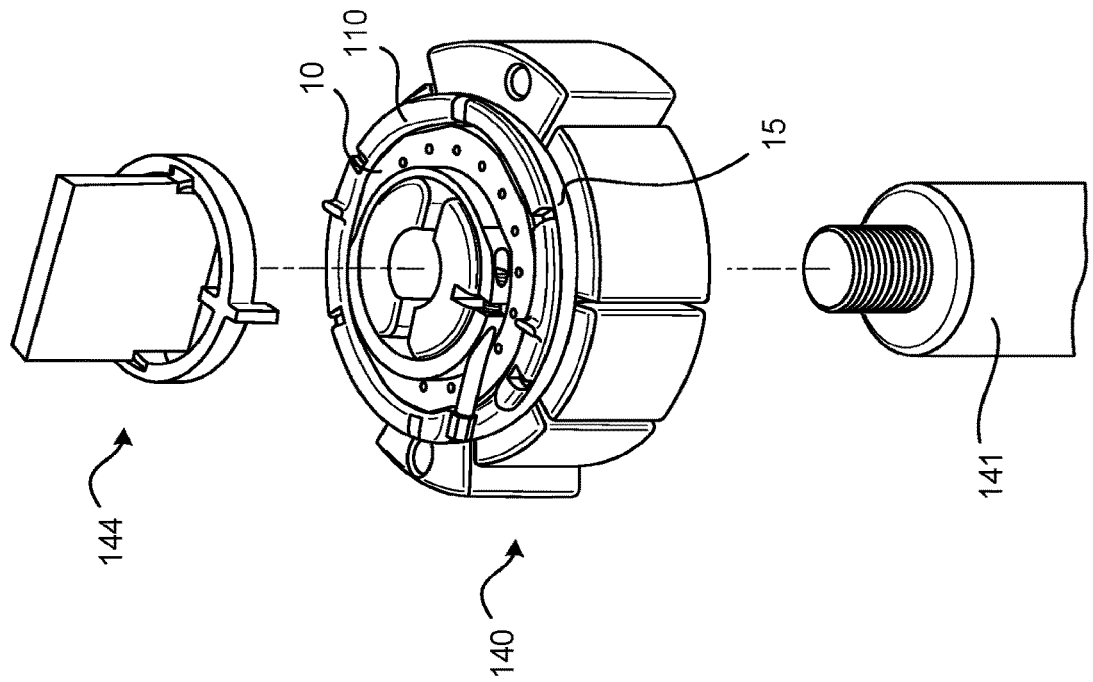
FIG. 7H is a perspective view of another step of a method of engaging a connection interface of an implantable anastomotic assembly to an apical cuff, in accordance with various embodiments.
Figure 7G:
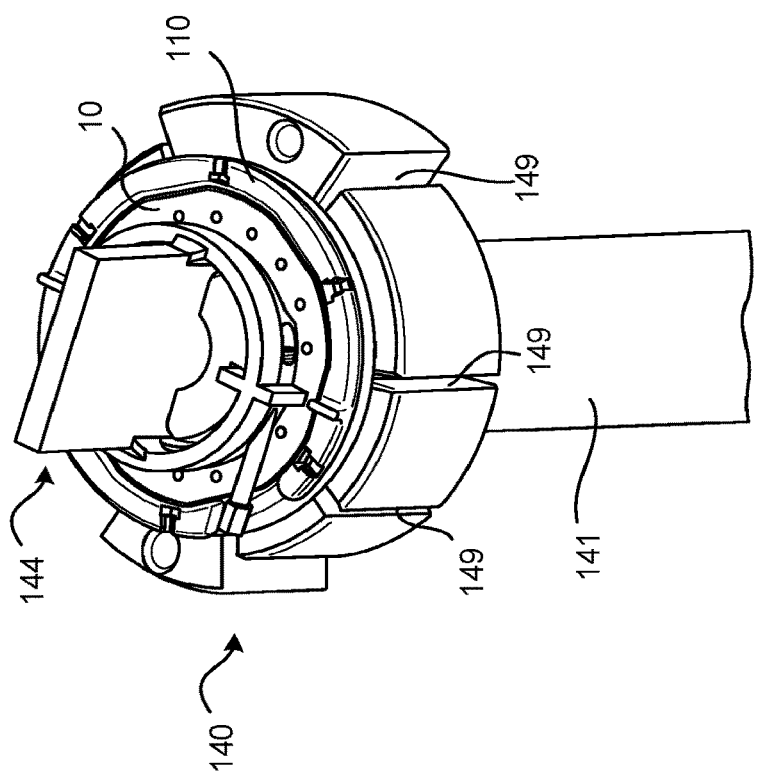
FIG. 7G is a perspective view of another step of a method of engaging a connection interface of an implantable anastomotic assembly to an apical cuff, in accordance with various embodiments.

In various embodiments, and with reference to FIGS. 7C and 7D, a connection interface press 150 is provided. The connection interface 110 is generally configured to be seated against the connection interface press 150. The connection interface press 150 may include one or more slots 155 that are configured to receive the alignment features 115 (FIG. 3) of the connection interface 110 described above, thereby holding the connection interface 110 in a known/controlled orientation within the connection interface press 150. The connection interface press 150 may also include a plurality of protrusions 153 that are configured to align with and partially extend into the apertures 113 of the connection interface 110, further ensuring proper alignment. In various embodiments, the connection interface press 150 may have one or more guide rods 158 that extend parallel to the tines 119 of the connection interface 110. Further, in various embodiments, the connection interface press 150 may define a channel 152 that is aligned with the gap 112 of the connection interface 110 in order to accommodate the tightening screw 12 of the apical cuff 10.

In various embodiments, and with reference to FIGS. 7E, 7F, 7G, and 7H, the method 690 may include mating the apical cuff press 140 with the connection interface press 150 in order to couple the apical cuff 10 to the connection interface 110. In various embodiments, the one or more guide rods 158 of the connection interface press 150 may be inserted within corresponding bores 148 of the apical cuff press 140 to properly align the two presses 140, 150 relative to each other. The tines 119 of the connection interface 110 pierce the sewing ring 15 and are subsequently received within the tine slots 149 of the apical cuff press 140. A compressive force may be applied between the two presses 140, 150 in order to secure/couple the apical cuff 10 to the connection interface 110. With the apical cuff 10 and the connection interface 110 coupled together, the connection interface press 150, the clocking key 144, and the handle 141 may be removed, leaving the apical cuff 10 and the connection interface 110 mated together. These two mated components may remain seated on the apical cuff press to protect the tines 119 in preparation for implantation of the assembly 100.

In various embodiments, and with reference to FIG. 8, a connector alignment module 160 is provided. The connector alignment module 160 is configured to hold the plurality of connectors 130 in the pre-installed longitudinal shape within a plurality of defined chambers 163, respectively. In various embodiments, the connector alignment module 160 may be provided with connectors 130 pre-installed with the connectors 130, or the connectors 130 may be loaded into a reusable connector alignment module 160. The cross-section of the chambers 163 may correspond to the cross-section of the connectors 130, thereby ensuring that the connectors 130 are in the proper/desired orientation. In various embodiments, the connector alignment module 160 may have a slightly tapered shape (e.g., 5-10 degrees from vertical) to affect the deployment trajectory of the connectors 130. The connector alignment module 160 may define one or more alignment bores 168 and a central hole for receiving a handle, as described in greater detail below. In various embodiments, the alignment bores 168 may have ball-spring detents to ensure the guide rods 178/188 (FIGS. 9A, 9B, 10A, 10B) are properly inserted within the alignment bores 168, as described in greater detail below. The connector alignment module 160 may also include a channel 162 for accommodating the tightening screw 12 of the apical cuff 10. In various embodiments, the bottom rim of the connector alignment module 160 includes a plurality of circumferentially distributed windows that enable a practitioner to see the connectors retained within the chambers 163, as well as one or more alignment features.

Figure 9A:
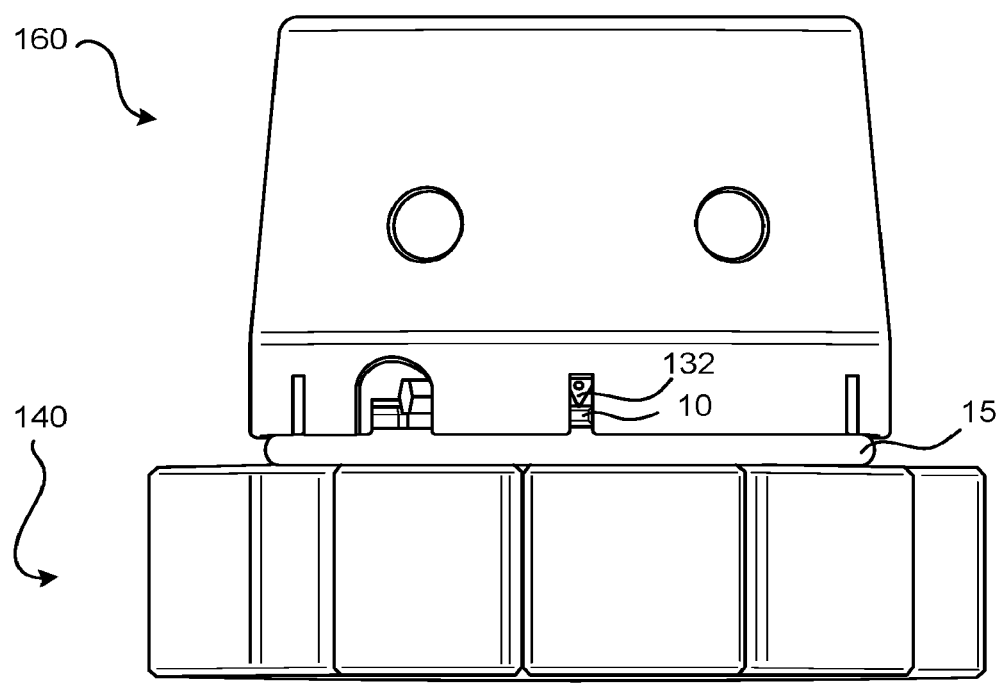
FIG. 9A is a perspective view of a step of a method of coupling a connection interface of an implantable anastomotic assembly to an apical cuff, in accordance with various embodiments.

In various embodiments, and with reference to FIG. 9A, the connector alignment module 160 may be engaged against the apical cuff press 140, with the apical cuff press 140 still having the mated apical cuff 10 and the connection interface 110 seated thereon. Alignment between the connector alignment module 160 and the mated cuff 10 and connection interface 110 may be achieved via engagement between the alignment features 115 (FIG. 3) of the connection interface 110 and corresponding alignment features defined in the bottom rim of the connector alignment module 160. With the connector alignment module 160 seated against the sewing ring 15 of the apical cuff, which itself is seated on the apical cuff press 140 with the connection interface 110, the distal ends 132 of the connectors 130 are positioned just above the sewing ring 15 and are ready to be deployed through the sewing ring.

Figure 9C:
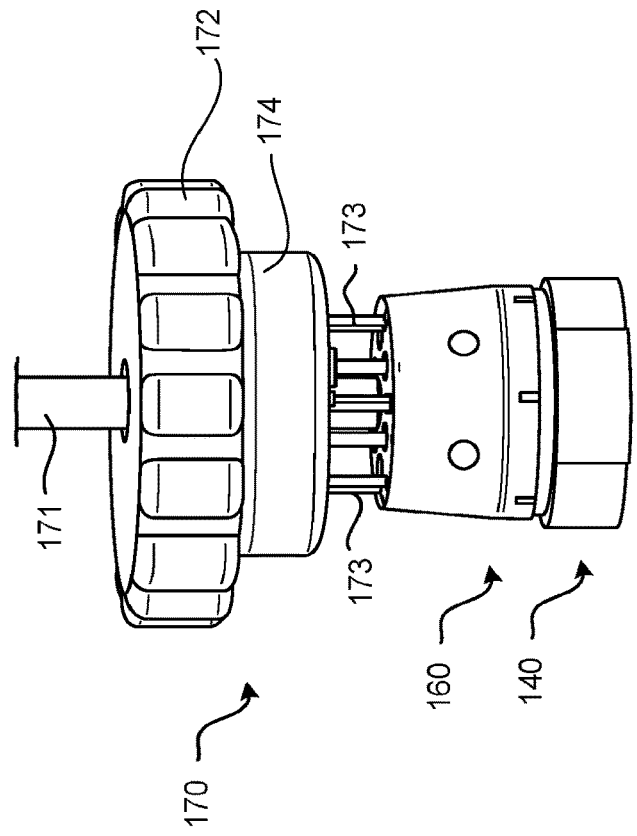
FIG. 9C is a perspective view of another step of a method of coupling a connection interface of an implantable anastomotic assembly to an apical cuff, in accordance with various embodiments.
Figure 9B:
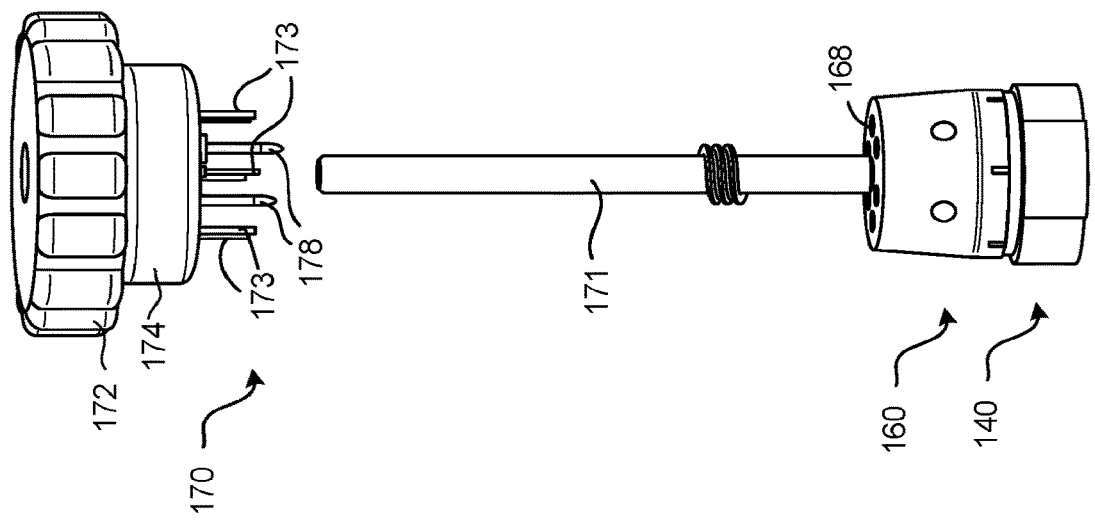
FIG. 9B is a perspective view of another step of a method of coupling a connection interface of an implantable anastomotic assembly to an apical cuff, in accordance with various embodiments.
Figure 9D:
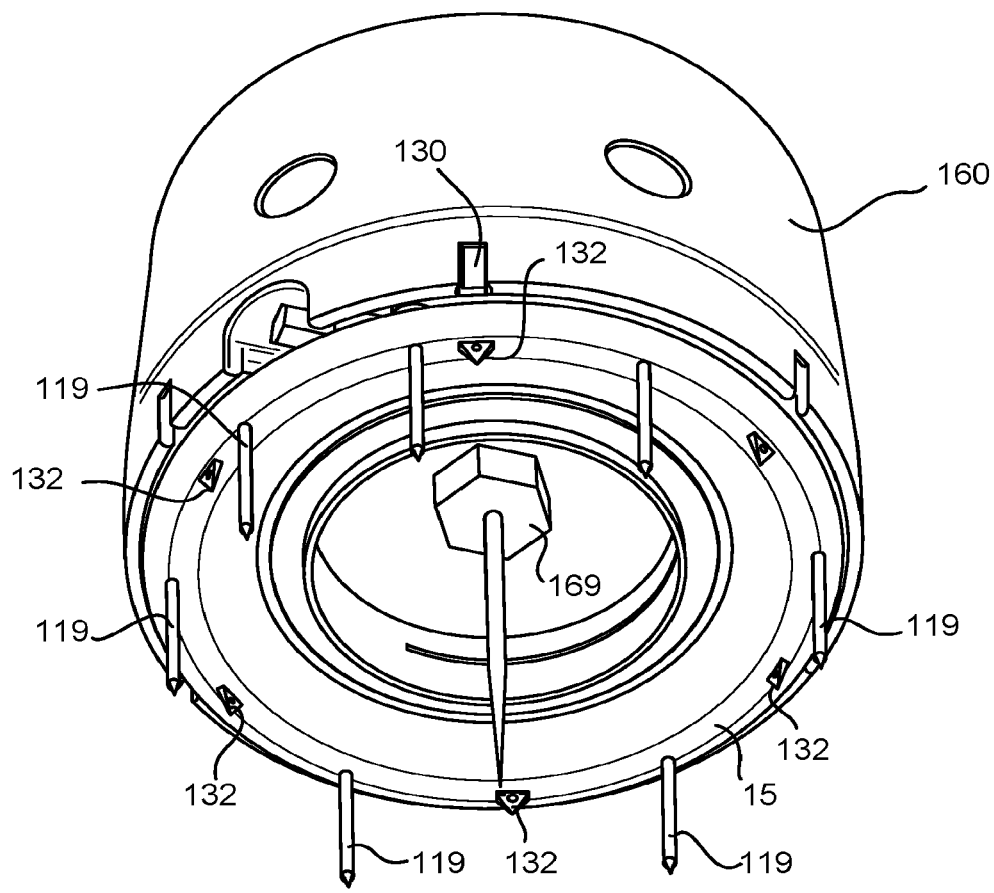
FIG. 9D is a perspective view of another step of a method of coupling a connection interface of an implantable anastomotic assembly to an apical cuff, in accordance with various embodiments.

In various embodiments, and with reference to FIGS. 9B, 9C, and 9D, the method 690 may include further securing and coupling the connection interface 110 to the apical cuff 10 by inserting the distal end 132 of the connectors 130 at least partially into the sewing ring 15 of the apical cuff 10. This step may be accomplished using a preliminary connector positioning tool 170. The preliminary connector positioning tool may include a shaft 171 that can be coupled to the central hole of the connector alignment module 160, a knob 172 that rotates to depress a piston 174 that is moveable along the shaft 171, and a plurality of pins 173 attached to the bottom of the piston 174. In response to rotation of the knob 172, which may threadably engage the shaft 171, the piston 174 may translate linearly down the shaft 171 such that the pins 173 push against the proximal end 131 of the connectors to partially eject the connectors 130 such that the distal end 132 of the connectors pierces the sewing ring 15 of the apical cuff. Guide rods 178 on the piston 174 may be received within alignment bores 168 to facilitate initial deployment. With the connectors 130 at least partially piercing the sewing ring 15, the preliminary connector positioning tool 170 may be removed. Further, a targeting needle 169 (FIG. 9D) may be coupled to a bottom portion of the connector alignment module 160, which may be useful for the subsequent step of engaging the apical cuff 10/connection interface 110 against the cardiovascular tissue.

Figure 10A:
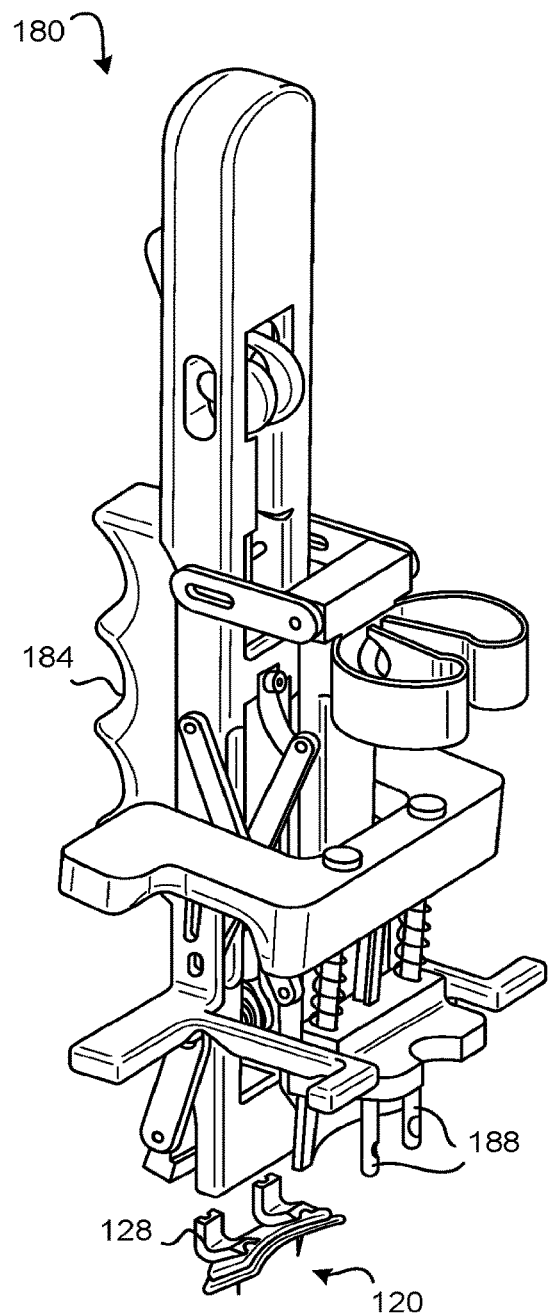
FIG. 10A is a perspective view of an implantation tool and an outer plate, in accordance with various embodiments.
Figure 10B:
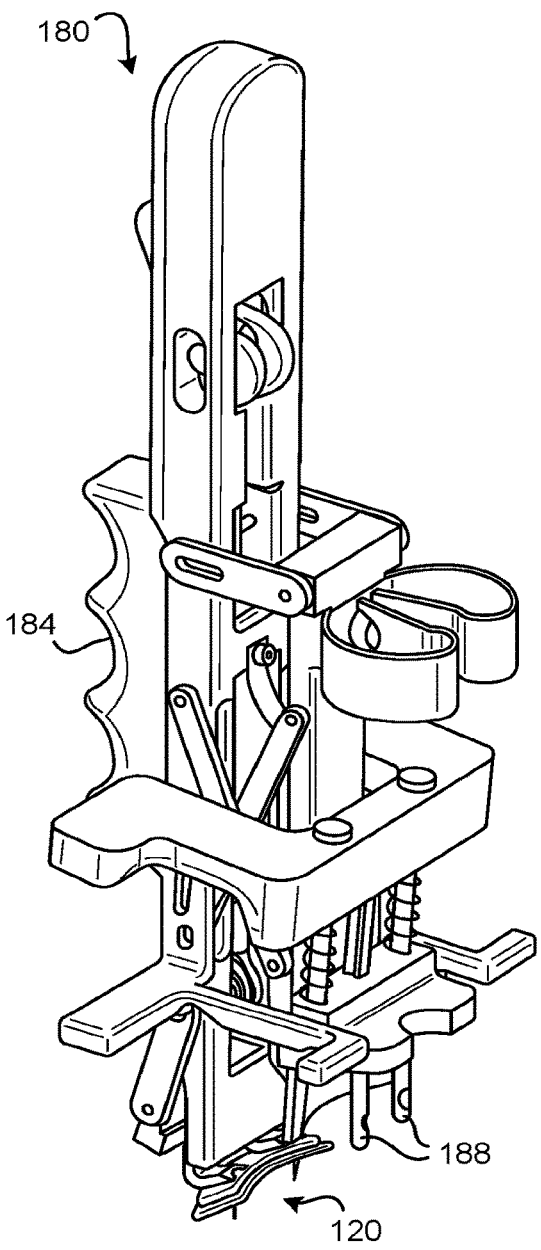
FIG. 10B is a perspective view of an outer plate coupled to an implantation tool, in accordance with various embodiments.

In various embodiments, and with reference to FIGS. 10A and 10B, an implantation tool is provided 180. The implantation tool 180 may be reusable, or may be a single-use device. Generally, the implantation tool 180 is configured to reversibly grasp an outer plate 120 (via interaction between the grasping elements 128 of the outer plate) in order to facilitate the step of engaging the outer plate 120 against the cardiovascular tissue at a known distance from the apical cuff 10/connection interface 110, as described in greater detail below. The implantation tool 180 may also enable controlled approximation/translation of the outer plate 120 toward the apical cuff 10/connection interface 110. Also, the implantation tool 180 may deploy the connectors 130 from the connector alignment module 160. The implantation tool 180 may include a hand grip 184 (e.g., an ergonomic grip) where a practitioner may grasp during use.

Figure 11A:
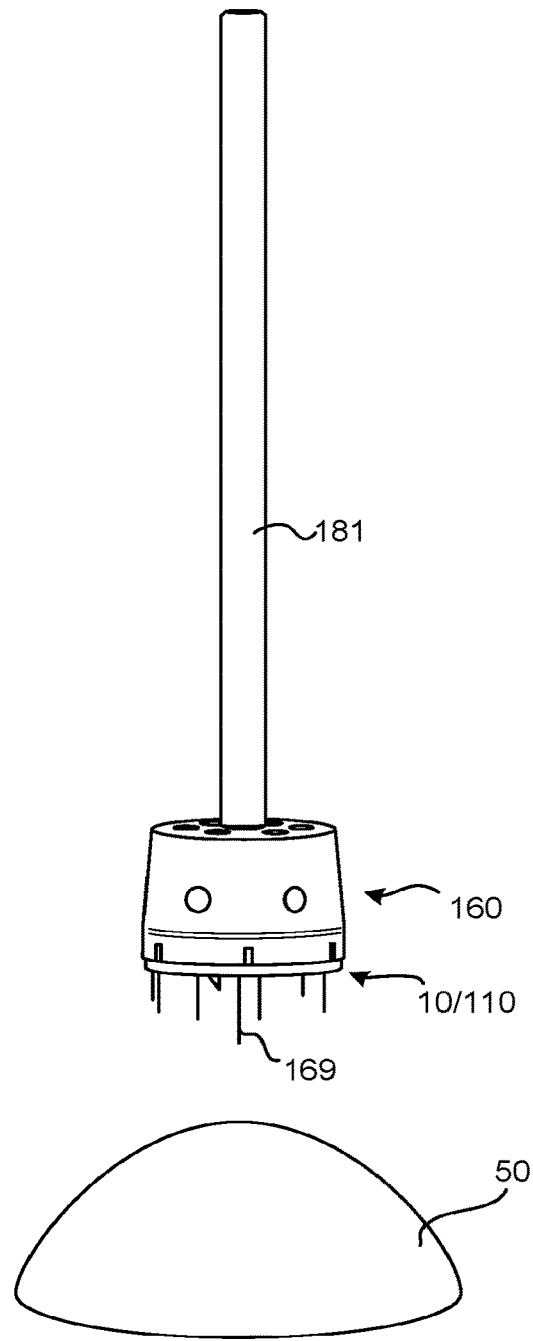
FIG. 11A is a perspective view of a step of a method of attaching an implantable anastomotic assembly to a ventricle, in accordance with various embodiments.
Figure 11B:
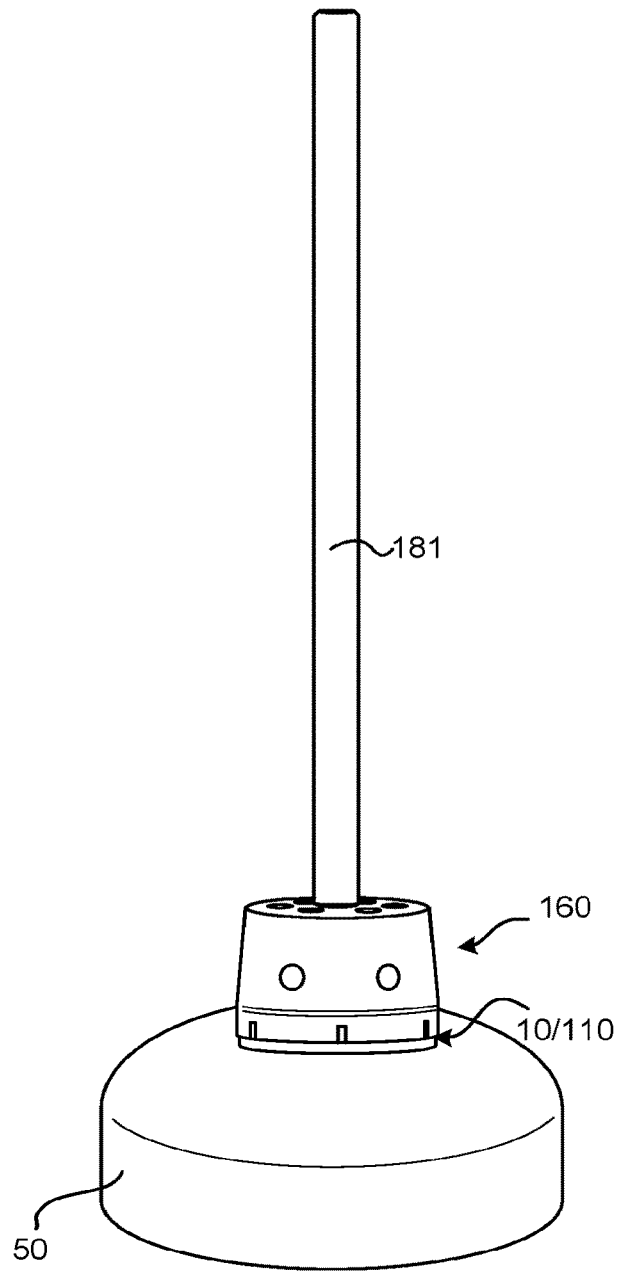
FIG. 11B is a perspective view of another step of a method of attaching an implantable anastomotic assembly to a ventricle, in accordance with various embodiments.
Figure 11C:
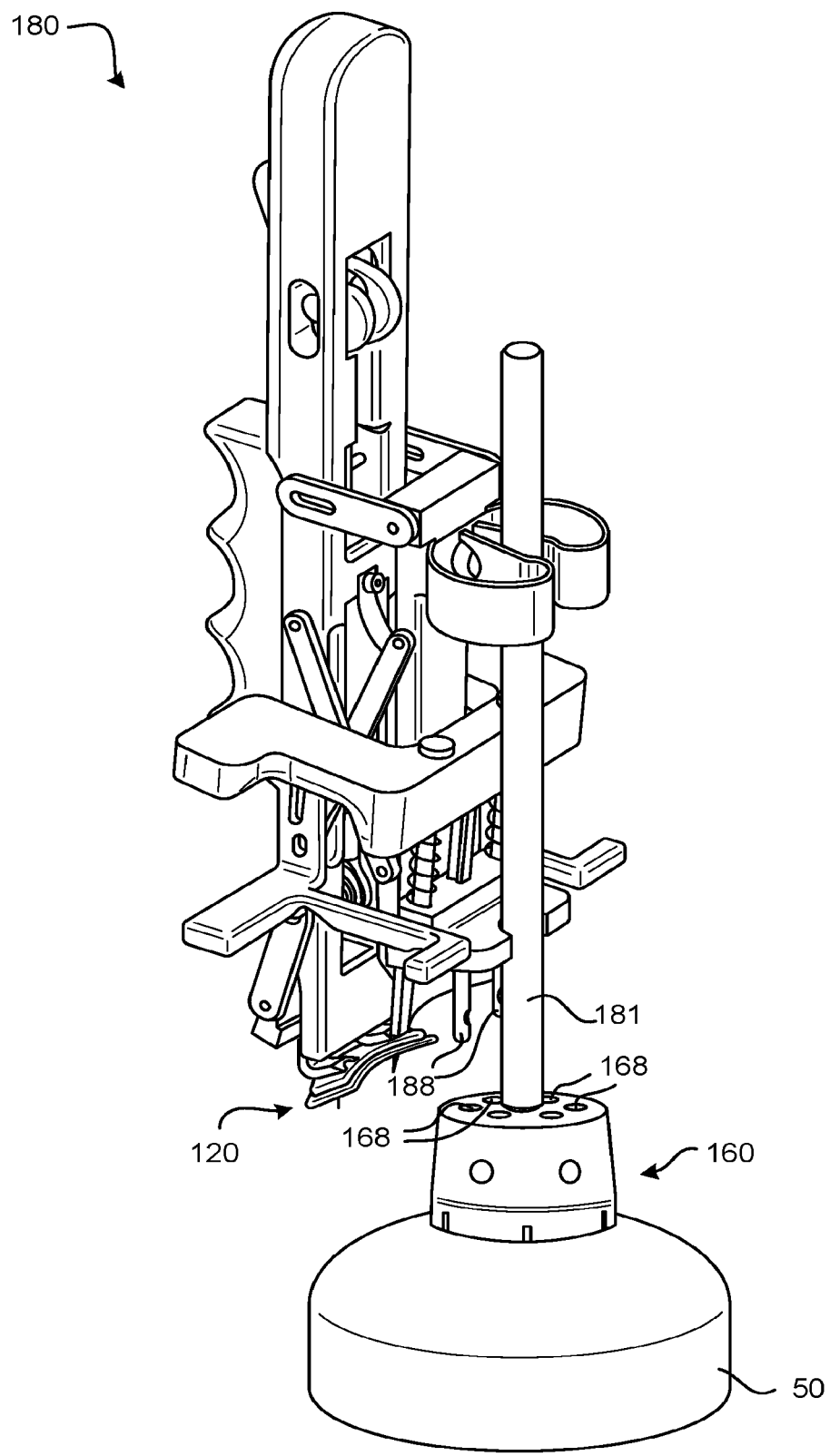
FIG. 11C is a perspective view of another step of a method of attaching an implantable anastomotic assembly to a ventricle, in accordance with various embodiments.
Figure 11E:
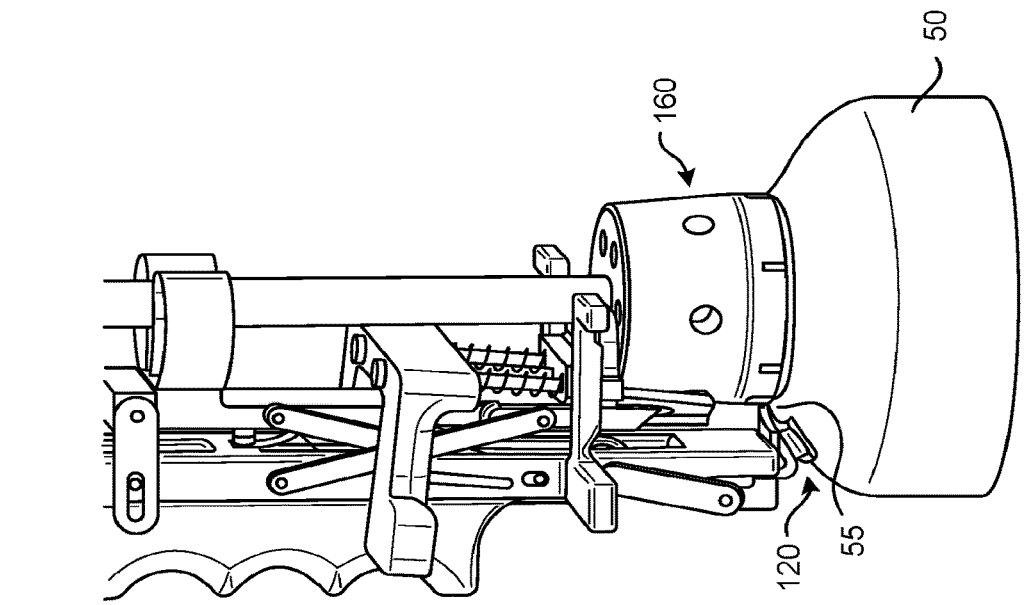
FIG. 11E is a perspective view of another step of a method of attaching an implantable anastomotic assembly to a ventricle, in accordance with various embodiments.
Figure 11D:
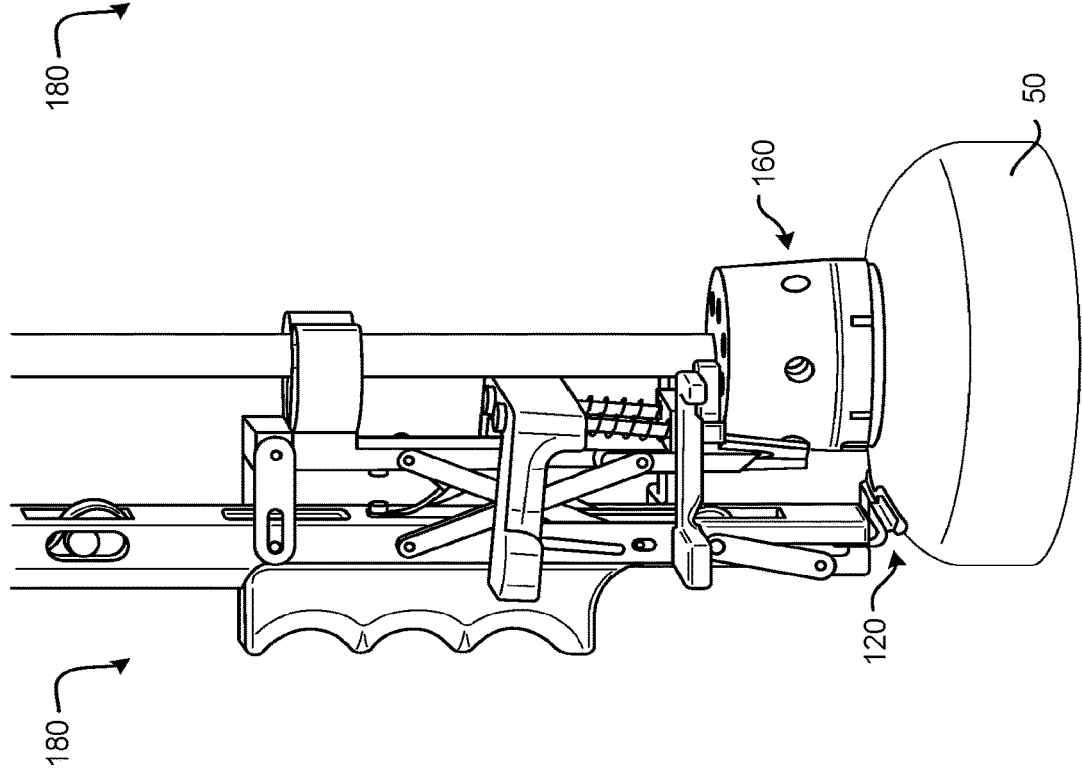
FIG. 11D is a perspective view of another step of a method of attaching an implantable anastomotic assembly to a ventricle, in accordance with various embodiments.
Figure 11F:
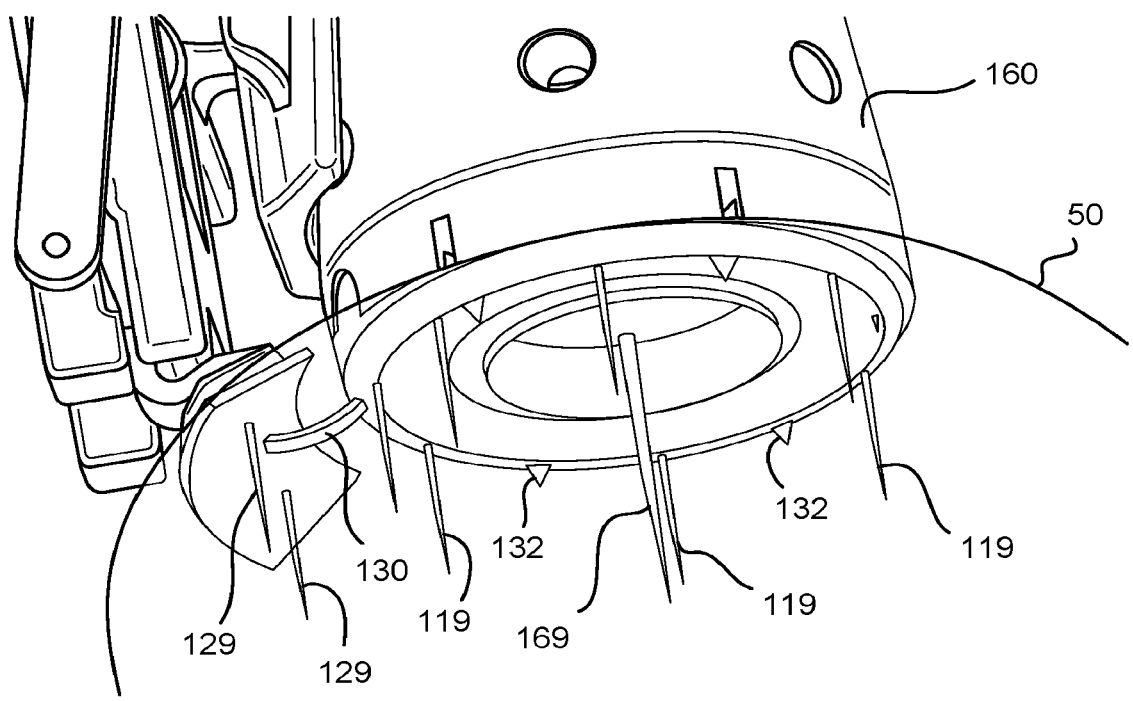
FIG. 11F is a perspective view of another step of a method of attaching an implantable anastomotic assembly to a ventricle, in accordance with various embodiments.

In various embodiments, and with reference to FIGS. 11A, 11B, 11C, 11D, 11E, and 11F, a handle 181 may be coupled to the central hole of the connector alignment module 160. The handle 181 may be grasped by a practitioner and the practitioner may direct the connector alignment module 160, with the apical cuff 10 and the connection interface 110 connected thereto, to a preferred location (e.g., an apex of the left ventricle), as shown in FIG. 11A. Using the targeting needle 169 as a guide, the practitioner may engage the apical cuff 10/connection interface 110 against the heart 50. Next, the implantation tool 180 may be coupled to the handle 181. The implantation tool 180 may include one or more alignment rods 188 that are configured to engage the alignment bores 168 of the connector alignment module 160. The implantation tool 180 may translate down the handle 181, the alignment rods 188 may be received within the corresponding alignment bores 168, and the outer plate 120, which is connected to the implantation tool 180, is pressed into engagement with the heart 50 (FIG. 11D).

In various embodiments, the implantation tool 180 includes a first actuating mechanism that enables the practitioner to controllably approximate the outer plate 120 (already engaged against the heart 50) toward the apical cuff 10/connection interface 110. This approximation motion may be a linear motion (as opposed to an arcuate, curved translation) and helps to form the gasket 55 of myocardium between the outer plate and the apical cuff 10/connection interface 110. The implantation tool 180 may further include a second actuating mechanism that is configured to deploy a connector 130 from a respective chamber of the connector alignment module 160. As previously described, this deployment causes the connector to transition from its pre-installed longitudinal shape to its installed longitudinal shape, thereby automatically redirecting the connector toward the outer plate 120 to be secured retained via the receptacle 123 of the outer plate. This process may be repeated for the remaining connectors and outer plates. In various embodiments, as mentioned above with reference to FIG. 6, multiple outer plates and connectors may be implanted simultaneously. After all of the outer plates are connected to the apical cuff 10/connection interface 110 via the connectors, the implantation tool 180 and the connector alignment module 160 may be removed, leaving the installed assembly 100 of FIG. 12. In various embodiments, the connectors 130 may be further tensioned as necessary.

Figure 13A:
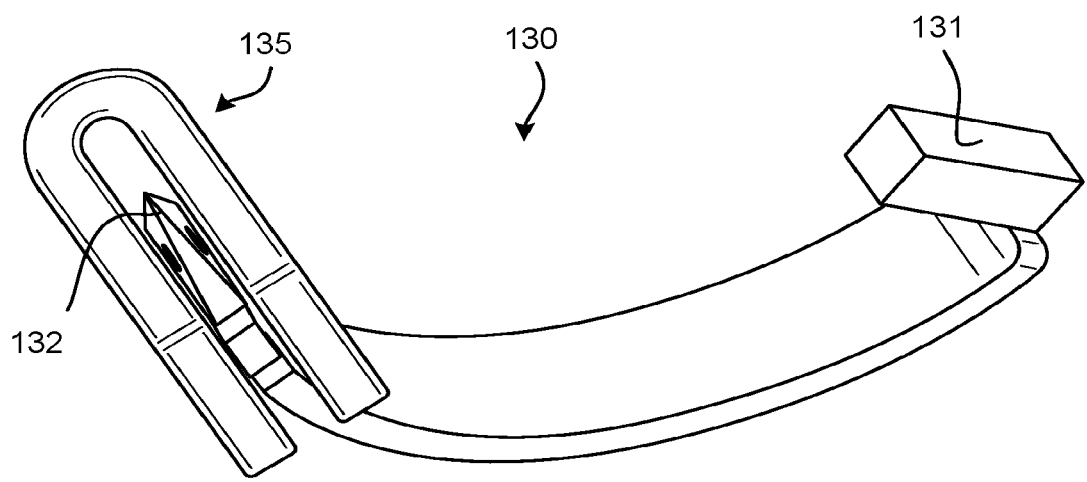
FIG. 13A is a perspective view of a cap covering a distal end of a connector of an implantable anastomotic assembly, in accordance with various embodiments.
Figure 13B:
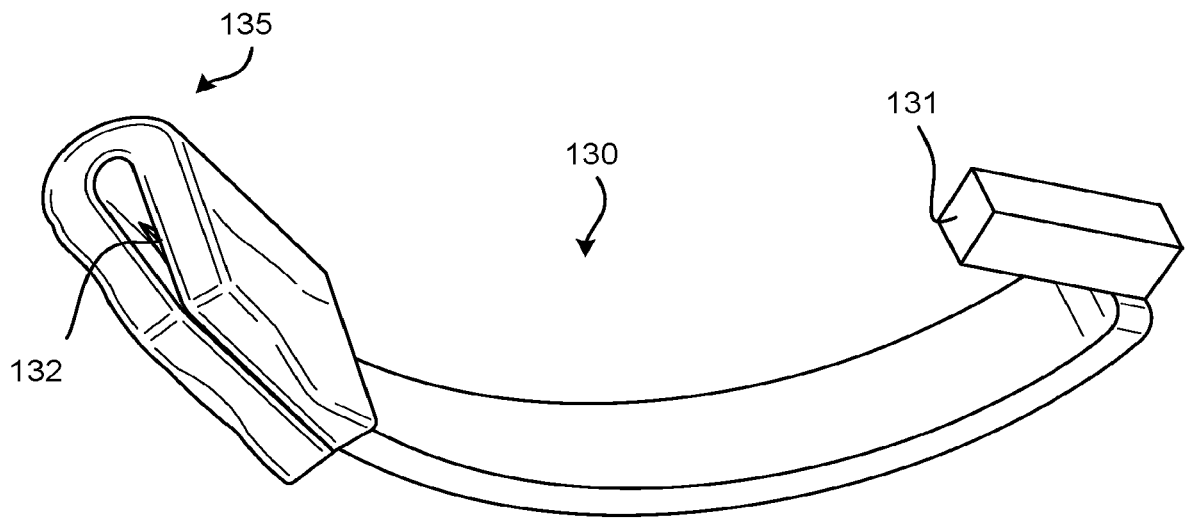
FIG. 13B is a perspective view of a crimped cap covering a distal end of a connector of an implantable anastomotic assembly, in accordance with various embodiments.

In various embodiments, and with reference to FIGS. 13A and 13B, the distal ends 132 (tips) of the connectors may be capped, cut, or crimped. For example, malleable caps 135 may be disposed around the distal ends 132 of the connectors 130. The malleable cap 135 covers the sharp tip of the distal end 132 of the connector 130 and may serve as a secondary means for securing the connectors.

In various embodiments, and with reference to FIGS. 14A and 14B, another implementation of the implantable anastomotic assembly 200 is provided. The implantable anastomotic assembly 200 generally includes a connection interface 210, a plurality of outer plates 220, and a plurality of connectors 230 that are configured to extend between and interconnect the connection interface 210 and the plurality of outer plates 220. The connection interface 210, as defined above, may refer to a support ring coupled to an apical cuff 10, or the connection interface may be modified apical cuff that includes the functionality/features of the combination of the apical cuff 10 and the connection interface 210. In various embodiments, the connectors 230 of the implantable anastomotic assembly 200 are configured to extend outside of the cardiovascular tissue (e.g., the connectors 230 are configured to not pierce the myocardium). Because of the externally extending connectors 230, the implantable anastomotic assembly 200 further includes one or more tissue anchors 205 to secure the assembly 200 to the cardiovascular tissue, according to various embodiments. FIG. 14A shows the tissue anchors 205 in a deployed/installed position, whereas FIG. 14B shows the tissue anchors in a pre-installed position, as described in greater detail below with reference to FIGS. 16A, 16B, and 17.

Figure 15:
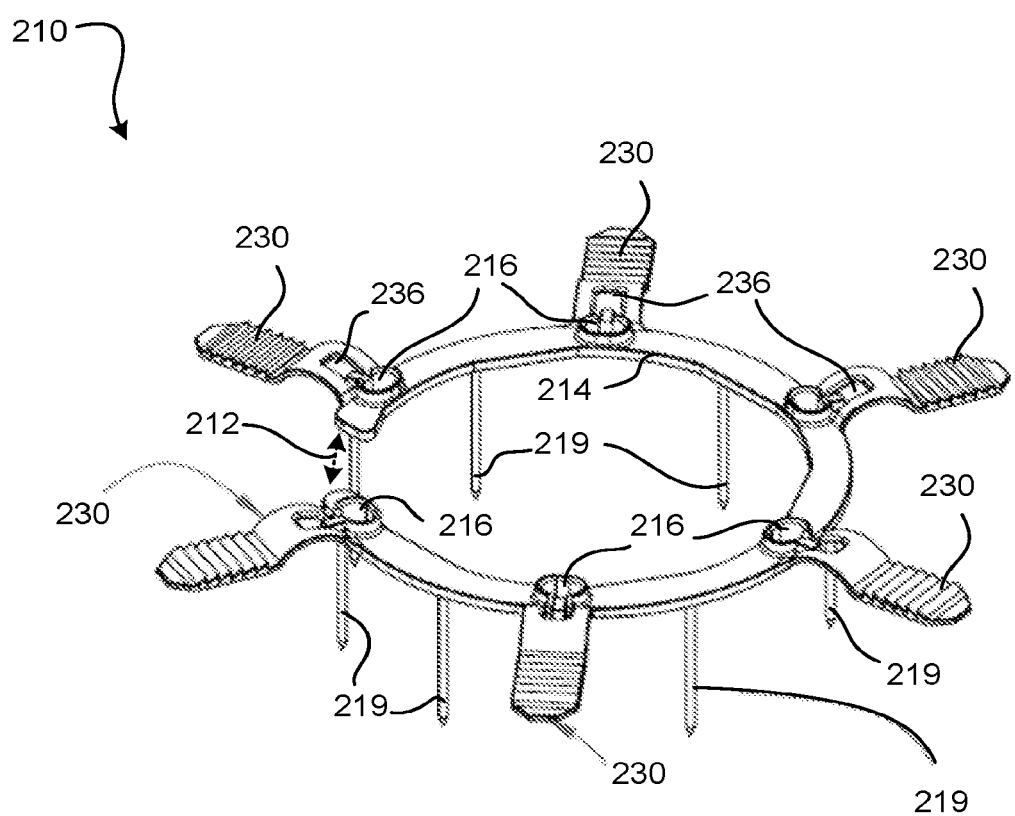
FIG. 15 is a perspective view of another implementation of a connection interface of an implantable anastomotic assembly, in accordance with various embodiments.

In various embodiments, and with reference to FIG. 15, the connection interface 210 is provided. As mentioned above, whereas the connection interface is repeatedly shown and described herein as being attachable to an apical cuff 10, the connection interface 210 of the implantable anastomotic assembly 200 may be a single product that incorporates the functionality/features of both the connection interface 210 and an apical cuff. The connection interface 210 may be referred to as a support ring, and may be configured to engage the apical cuff 10. The connection interface 210 may be a single, unitary component, or the connection interface may be comprised of multiple arcuate segments. The connection interface may have a continuous ring structure, or the connection interface 210 may be a partial ring in that a gap 212 is defined between ends of the ring structure. The gap 212, according to various embodiments, may be used to align the connection interface 210 with one or more features of the apical cuff. For example, the gap 212 may accommodate the tightening screw 12 of the apical cuff 10.

The connection interface 210 may be made from a metallic material. The connection interface 210 may have a surface 214 that is configured to complement a corresponding surface (e.g., edge 14) of the apical cuff 10 to further promote secure engagement between the apical cuff 10 and the connection interface 210. The connection interface 210 may define a plurality of anchor windows 216 through which the tissue anchors 205 are configured to be inserted, as described in greater detail below with reference to FIGS. 16A, 16B, and 17. The connection interface 210 may comprise a plurality of tines 219 that extend from a bottom surface of the connection interface 210, with the tines 219 being configured to facilitate retention of the connection interface 210 and to help distribute force after the connection interface 210 is installed against the cardiovascular tissue. The number of anchor windows 216 and the number of tines 219 is not limited to the number shown in the figures. That is, the number of anchor windows 216 and tines 219 may be selected according to the specifics of a given application.

In various embodiments, the plurality of connectors 230 are connection tabs that extend from and are coupled to the connection interface 210. Each connector of the plurality of connectors 230 has ridges or other engagement structures that are configured to engage with a corresponding retention feature on a respective outer plate of the plurality of outer plates, in accordance with various embodiments. Though these connectors 230 are described in greater detail below with reference to FIG. 18, generally the connectors 230 are configured to extend external to the cardiovascular tissue (see FIG. 14A) and are configured to interconnect the connection interface 210 and the plurality of outer plates 220 after the connection interface 210 and respective outer plates 220 are engaged against the cardiovascular tissue. In various embodiments, and with reference to FIGS. 14A, 15, and 17, each connector of the plurality of connectors 230 extends from the connection interface 210 proximate one of the anchor windows 216. In various embodiments, each connector of the plurality of connectors 230 defines a hook window 236 at or near the junction between the connector 230 and the connection interface 210. As described in greater detail below, the tissue anchors 205 are generally configured to be inserted through the anchor windows 216, and a proximal end of each tissue anchor 205 is configured to be retained within a respective hook window 236 of the connector.

Figure 16A:
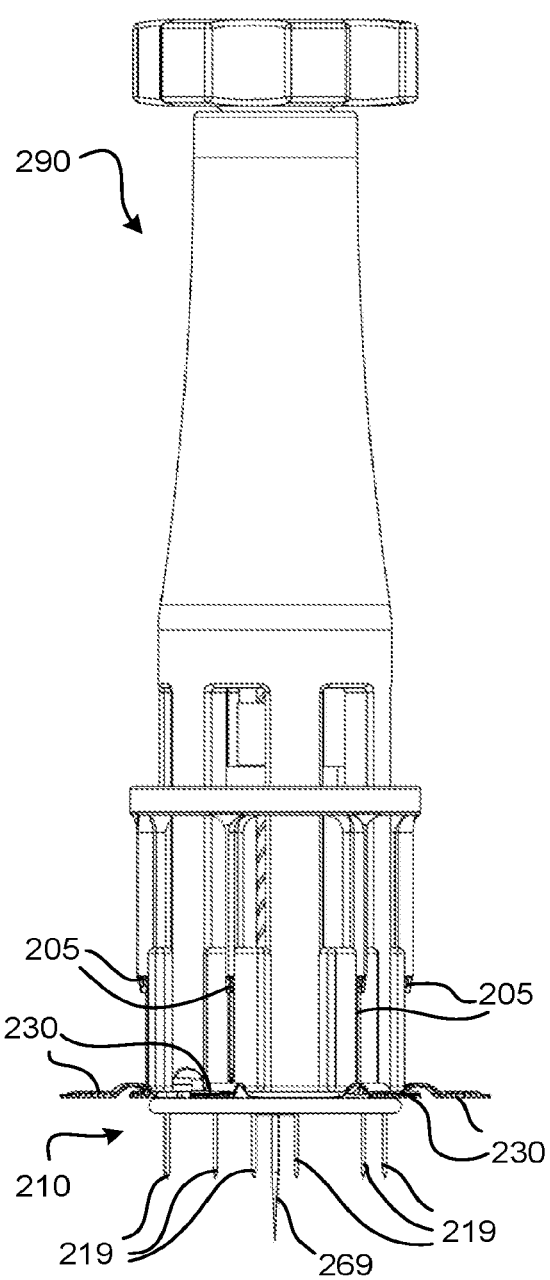
FIG. 16A is a perspective view of an anchor deployment tool showing tissue anchors in a pre-deployed state, in accordance with various embodiments.
Figure 16B:
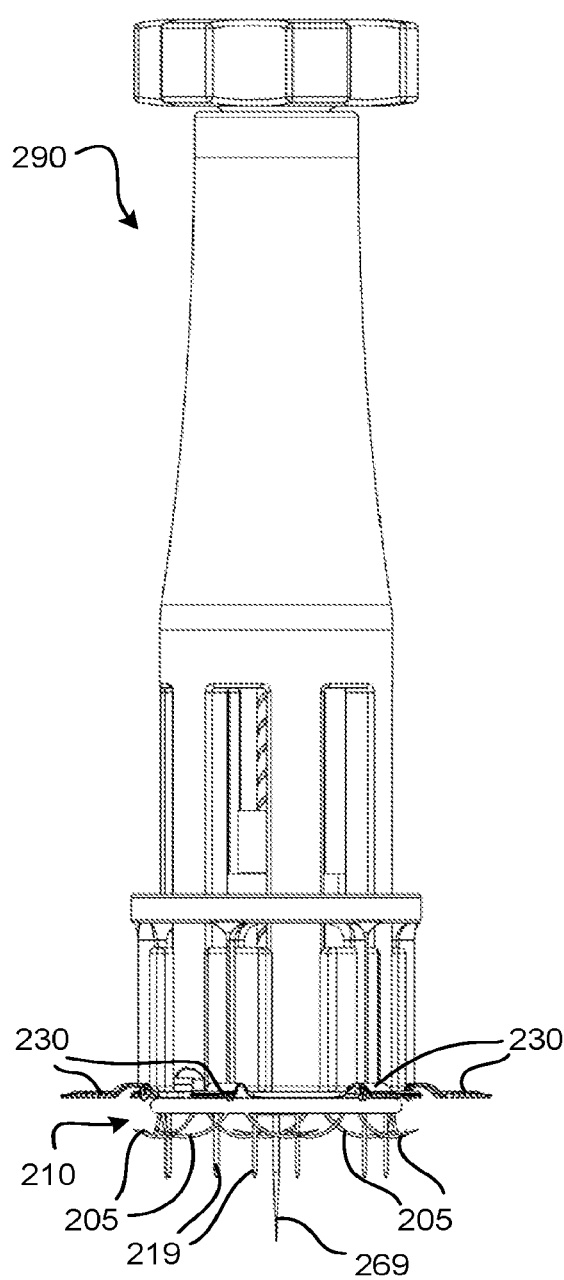
FIG. 16B is a perspective view of an anchor deployment tool showing tissue anchors at least partially deployed, in accordance with various embodiments.
Figure 17:
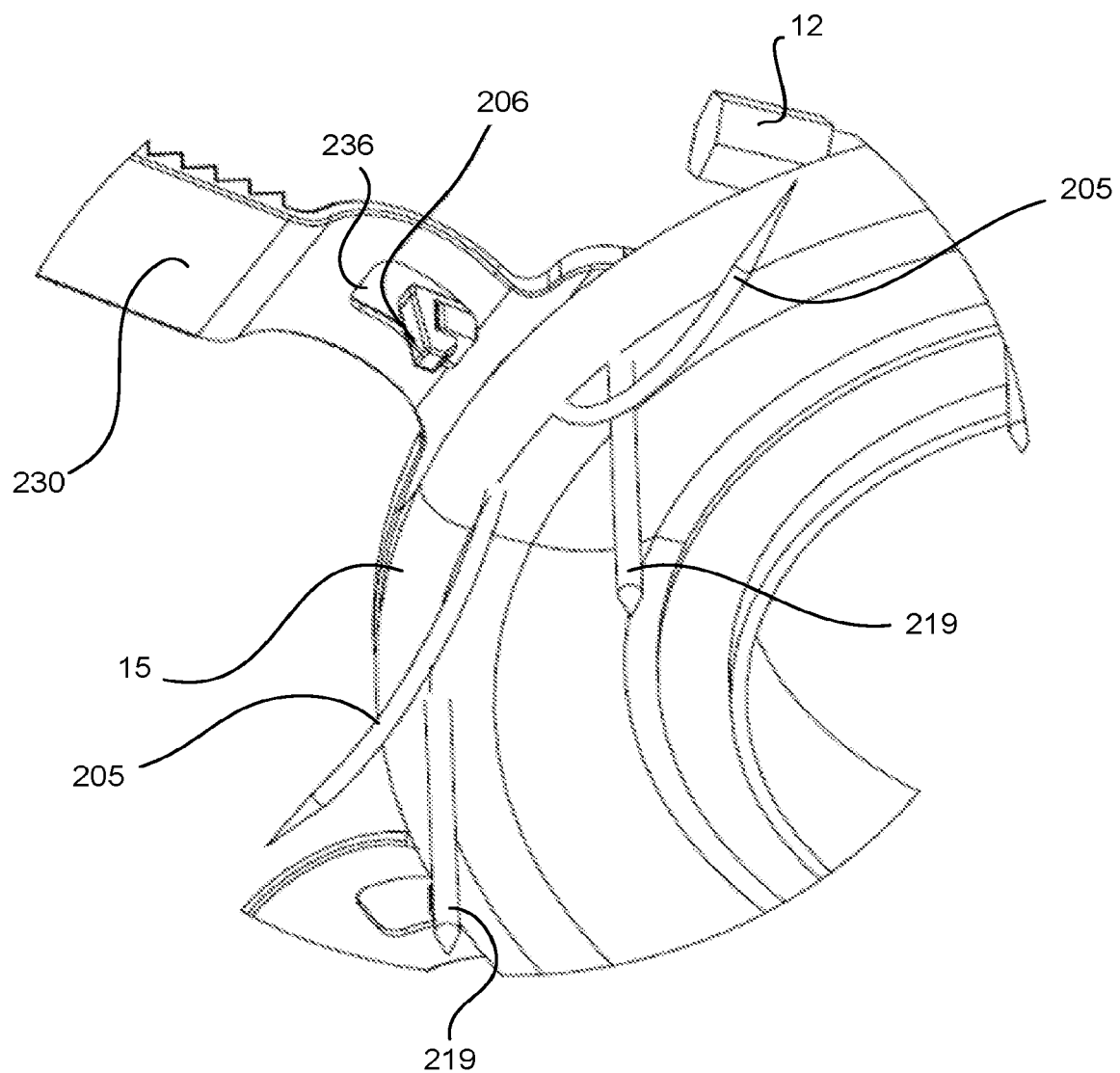
FIG. 17 is a perspective view of a tissue anchor of a connection interface of an implantable anastomotic assembly, in accordance with various embodiments.

In various embodiments, and with reference to FIGS. 16A, 16B, and 17, a tissue anchor deployment tool 290 is provided, and deployment of the tissue anchors 205 is shown. In various embodiments, the tissue anchors 205 may be made from a shape memory material, such as nitinol, beta titanium, or other medical grade material with superelastic and/or shape memory properties. In various embodiments, the tissue anchors 205 may be configured to assume a specific shape/orientation in response to deployment of the tissue anchors 205 from the tissue anchor deployment tool 290. That is, the tissue anchor deployment tool 290 may define a plurality of chambers within which the tissue anchors 205 may be loaded (see FIG. 16A), and the tissue anchor deployment tool 290 may include an actuation mechanism that, in response to be actuated by a practitioner, causes the tissue anchors 205 to be ejected from the chambers of the tissue anchor deployment tool 290. In various embodiments, the tissue anchors 205 have a non-circular cross-sectional shape (e.g., rectangular shape), which may facilitate directional control of the tissue anchors 205 during deployment by being held/retained within the tissue anchor deployment tool 290 in the proper orientation.

In various embodiments, and with continued reference to FIGS. 16A, 16B, and 17, before the tissue anchors 205 are deployed from the tissue anchor deployment tool 290, the apical cuff 10 may be seated against the connection interface 210. Accordingly, in response to actuation of the tissue anchor deployment tool 290, the tissue anchors 205 may extend through the anchor windows 216 defined by the connection interface 210, through the sewing ring 15 of the apical cuff 10, and into the cardiovascular tissue (see FIG. 17). In response to deployment, the tissue anchors 205 may be configured to automatically transition from a pre-installed longitudinal shape (e.g., linear, FIG. 16A) to an installed longitudinal shape (e.g., non-linear, curved, FIG. 16B) after they are inserted through the cardiovascular tissue. In various embodiments, the tissue anchors may maintain a curved longitudinal shape after being installed. In various embodiments, the tendency of the tissue anchors 205 to assume their programmed, desired longitudinal shape causes the tissue anchors 205 to redirect within the cardiovascular tissue, securely anchoring the connection interface 210. In various embodiments, the tissue anchor deployment tool 290 may include a central hole that accommodates targeting needle 269, which guides placement of the connection interface 210/apical cuff 10 against the cardiovascular tissue before deployment of the tissue anchors 205.

In various embodiments, and with specific reference to FIG. 17, the proximal end of the tissue anchors 205 may comprise a hook 206 or other such engagement feature, and this hook 206 may be received within the hook window 236 defined in the connector 230. Accordingly, the tissue anchors 205 may not only anchor the connection interface 210 to the cardiovascular tissue, the tissue anchors 205 may provide a degree of retention/securement to the connectors 230 in order to help the connectors 230 remain coupled to the outer plates 220, as described in the following paragraph with reference to FIG. 18.

Figure 18:
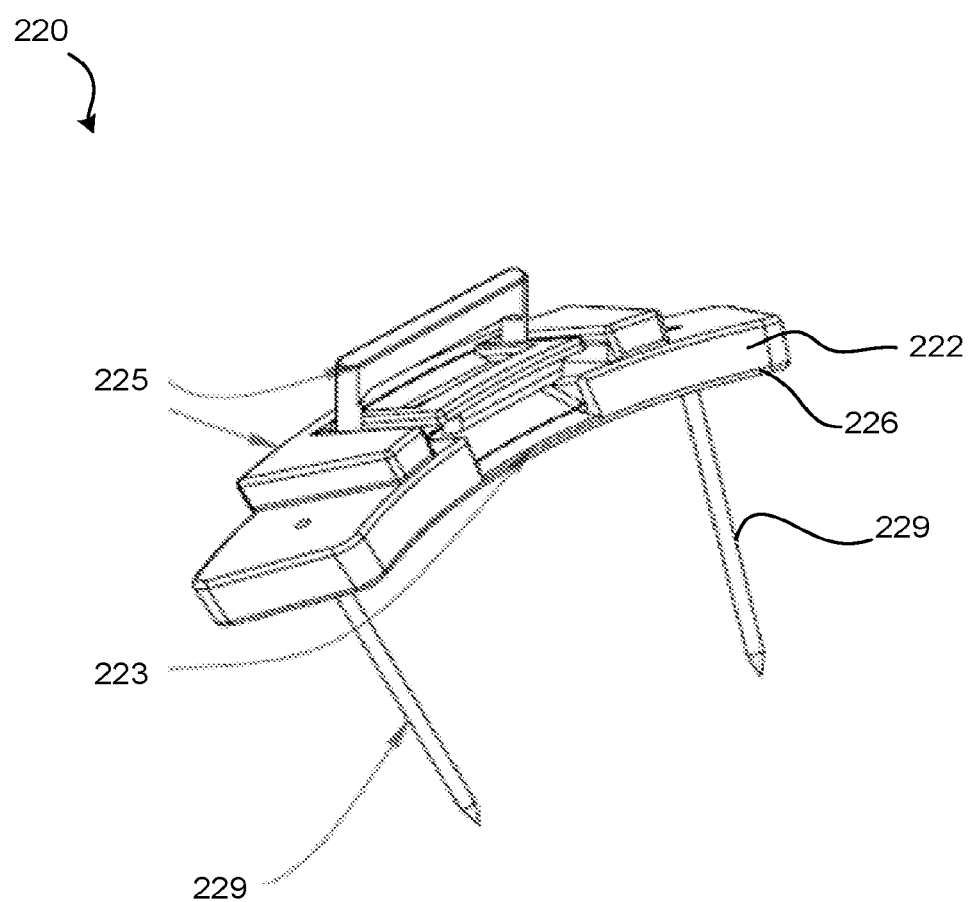
FIG. 18 is a perspective view of another implementation of an outer plate of an implantable anastomotic assembly, in accordance with various embodiments.

In various embodiments, and with reference to FIG. 18, one outer plate 220 of the plurality of outer plates is provided. As mentioned above, the number of outer plate 220 is not limited to the number depicted in the figures (six), and thus the implantable anastomotic assembly 200 may have more or less. For example, in various embodiments the implantable anastomotic assembly 200 may have two or more outer plates (with a corresponding number of connectors, or with multiple connectors for each outer plate). In various embodiments, the implantable anastomotic assembly may include a single, ring-like outer plate. In various embodiments, each outer plate 220 comprises a body 222. The body 222 may be curved in two directions. That is, the body 222 of each outer plate 220 may form an arcuate segment of a ring shape that extends around and is generally concentric with the connection interface 210 in response to the implantable anastomotic assembly 200 being in the installed position (see FIG. 14A). The body 222 of each outer plate 220 may also have a bottom surface that is concave, thereby conforming to the epicardial surface of myocardium of the ventricle. In various embodiments, the bottom surface (e.g., the concave bottom surface) may have a buttress material 226, such as a felt or polytetrafluoroethene, that helps to prevent tearing of the epicardium and to improve hemostasis between the outer plate 220 and the epicardium.

In various embodiments, each outer plate 220 may include one or more tines 229 that extend from the bottom surface of the outer plate 220 and impale the epicardial surface and embed in the myocardium. The purpose of the tines 229 is to equalize the distribution of central compressive forces that push the intervening myocardium against the apical cuff to achieve hemostasis.

In various embodiments, each outer plate 220 defines a receptacle 223 configured to receive a portion of the connector 230 (i.e., connection tab). In various embodiments, each outer plate 220 also defines a retention feature 225, such as a ratcheting mechanism, that is configured to retain the portion of the connector 230. For example, each connector 230 of the plurality of connectors may be configured to be inserted through a respective receptacle 223 of a respective outer plate 220 in response to approximation/translation of the outer plate 220 toward the connection interface 210, as described above. In various embodiments, the retention feature 225 of each outer plate 220 may employ a pawl, ball-wedge, cams, or other one-way locking mechanisms. Further tensioning of the connectors 230 may be achieved after the outer plate 220 has been approximated. As mentioned above, the approximation step may create a myocardial gasket, and the connectors 230 may be configured to have a slight curve in order to accommodate the bulge/gasket. In various embodiments, the engagement between the connector 230 and the outer plate 220 may be reversed if, for example, removal of the outer plate 220 is warranted.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. An implantable anastomotic assembly that is configured to be attached to cardiovascular tissue, the implantable anastomotic assembly comprising:
   an apical cuff; and
   at least one of a plurality of plates circumscribing a circumferential aspect of the apical cuff and configured to be attached to the cardiovascular tissue and compress the cardiovascular tissue with the apical cuff.

2. The implantable anastomatic assembly of claim 1, further comprising a connection interface, the connection interface being either an integral part of the apical cuff or configured to couple to the apical cuff.

3. The implantable anastomotic assembly of claim 2, wherein the at least one of the plurality of plates couple to the connection interface.

4. The implantable anastomotic assembly of claim 3, wherein the connection interface further comprises a plurality of apertures, each of the at least one of a plurality of plates has a receptacle; and further comprising a plurality of connectors, each being configured to be coupled between a respective aperture of the plurality of apertures of the connection interface and engage with a respective aperture of the plurality of apertures of the connection interface.

5. The implantable anastomotic assembly of claim 4, wherein the plurality of connectors comprise superelastic material.

6. The implantable anastomotic assembly of claim 4, wherein each connector of the plurality of connectors comprises a distal end comprising one or more retention features configured to engage the receptacle of a respective plate of the plurality of outer plates.

7. The implantable anastomotic assembly of claim 6, wherein each connector of the plurality of connectors comprises a tab configured to engage the connection interface adjacent the respective aperture.

8. The implantable anastomotic assembly of claim 6, wherein the plurality of connectors are configured to extend into the cardiovascular tissue.

9. The implantable anastomotic assembly of claim 7, wherein each of the plurality of plates further comprises a ratcheting mechanism configured to receive a portion of the connection tab.

10. The implantable anastomotic assembly of claim 1, wherein each of the at least one of a plurality of outer plates further comprises at least one tissue anchor configured to engage the cardiovascular tissue.

11. The implantable anastomotic assembly of claim 1, wherein each of the at least one of a plurality of outer plates is an arcuate segment having a surface configured to engage the cardiovascular tissue.

12. The implantable anastomotic assembly of claim 1, wherein a plate of the plurality of outer plates is configured to be engaged against the cardiovascular tissue.

13. A ventricular assist system comprising:
   a. an implantable anastomotic assembly that is configured to be attached to a ventricle, implantable the anastomotic assembly comprising:
      1. An apical cuff;
      2. A plurality of plates configured to circumscribe a circumferential aspect of the apical cuff; and
   b. a connector alignment module configured to hold the apical cuff and the plurality of plates in a pre-installed association with each other; and
   c. an implantation tool configured to at least one of successively approximate the plurality of plates relative to the apical cuff and deploy the apical cuff and plurality of plates from the connector alignment module.

14. The ventricular assist system of claim 13, further comprising a connection interface comprising a support ring, wherein the ventricular assist system further comprises an assembly tool configured to facilitate coupling the support ring to the apical cuff.

15. The ventricular assist system of claim 13, wherein the connector alignment module is separate from and non-contiguous with the plurality of plates.

16. The ventricular assist system of claim 13, wherein a plate of the plurality of plates is configured to be engaged against the cardiovascular tissue.

* * * * *